US010449228B2

(12) United States Patent
Anderson

(10) Patent No.: US 10,449,228 B2
(45) Date of Patent: Oct. 22, 2019

(54) DOSAGE OF A GLUTEN PEPTIDE COMPOSITION

(71) Applicant: ImmusanT, Inc., Cambridge, MA (US)

(72) Inventor: Robert P. Anderson, Shrewsbury, MA (US)

(73) Assignee: ImmusanT, Inc., Cambridge, MA (US)

( * ) Notice: Subject to any disclaimer, the term of this patent is extended or adjusted under 35 U.S.C. 154(b) by 0 days.

(21) Appl. No.: 15/021,059

(22) PCT Filed: Sep. 10, 2014

(86) PCT No.: PCT/US2014/054959
§ 371 (c)(1),
(2) Date: Mar. 10, 2016

(87) PCT Pub. No.: WO2015/038624
PCT Pub. Date: Mar. 19, 2015

(65) Prior Publication Data
US 2016/0220629 A1 Aug. 4, 2016

Related U.S. Application Data

(60) Provisional application No. 62/014,666, filed on Jun. 19, 2014, provisional application No. 61/983,989, filed on Apr. 24, 2014, provisional application No. 61/876,172, filed on Sep. 10, 2013.

(51) Int. Cl.
*A61K 38/10* (2006.01)
*G01N 33/68* (2006.01)
*A61K 9/00* (2006.01)
*A61K 9/08* (2006.01)

(52) U.S. Cl.
CPC ............ *A61K 38/10* (2013.01); *A61K 9/0021* (2013.01); *A61K 9/08* (2013.01); *G01N 33/6866* (2013.01); *G01N 2333/55* (2013.01); *G01N 2333/57* (2013.01)

(58) Field of Classification Search
None
See application file for complete search history.

(56) References Cited

U.S. PATENT DOCUMENTS

| | | | |
|---|---|---|---|
| 4,740,371 A | 4/1988 | St. Remy et al. |
| 5,128,270 A | 7/1992 | Delacroix et al. |
| 5,334,504 A | 8/1994 | Wood et al. |
| 5,494,799 A | 2/1996 | Wood et al. |
| 5,547,669 A | 8/1996 | Rogers et al. |
| 5,750,356 A | 5/1998 | Spack et al. |
| 5,846,740 A | 12/1998 | Tobin et al. |
| 5,998,366 A | 12/1999 | Tobin et al. |
| 6,218,132 B1 | 4/2001 | Spack et al. |
| 6,300,308 B1 | 10/2001 | Schroit |
| 6,455,267 B1 | 9/2002 | Tobin et al. |
| 6,759,234 B1 | 7/2004 | Gefter et al. |
| 6,806,354 B2 | 10/2004 | Schroit |
| 7,094,555 B2 | 8/2006 | Kwok et al. |
| 7,144,569 B1 | 12/2006 | Anderson et al. |
| 7,202,216 B2 | 4/2007 | Sollid et al. |
| 7,303,871 B2 | 12/2007 | Hausch et al. |
| 7,361,480 B2 | 4/2008 | Maki et al. |
| 7,462,688 B2 | 12/2008 | Khosla et al. |
| 7,563,864 B2 | 7/2009 | Marti et al. |
| 7,604,957 B2 | 10/2009 | Fine |
| 7,608,392 B2 | 10/2009 | Rothel et al. |
| 7,888,460 B2 | 2/2011 | Anderson et al. |
| 8,053,235 B2 | 11/2011 | Buckner et al. |
| 8,329,144 B2 | 12/2012 | Anderson et al. |
| 8,378,072 B2 | 2/2013 | Bonnin |
| 8,426,145 B2 | 4/2013 | Khosla et al. |
| 8,835,603 B2 | 9/2014 | Anderson et al. |
| 9,464,120 B2 | 10/2016 | Anderson et al. |
| 2003/0215438 A1 | 11/2003 | Hausch et al. |
| 2005/0014205 A1 | 1/2005 | Rothel et al. |
| 2005/0249719 A1 | 11/2005 | Shan et al. |
| 2005/0256054 A1 | 11/2005 | Sollid et al. |
| 2006/0024334 A1 | 2/2006 | Larche et al. |
| 2006/0154853 A1 | 7/2006 | Steptoe et al. |
| 2006/0178299 A1 | 8/2006 | Anderson et al. |
| 2006/0189540 A1 | 8/2006 | Khosla et al. |
| 2006/0240475 A1 | 10/2006 | Khosla et al. |
| 2006/0286601 A1 | 12/2006 | Marti et al. |
| 2008/0145837 A1 | 6/2008 | Paulie et al. |
| 2008/0175971 A1 | 7/2008 | Anderson et al. |
| 2008/0318852 A1 | 12/2008 | Anderson et al. |
| 2009/0053297 A1 | 2/2009 | Balu-Iyer et al. |
| 2009/0156490 A1 | 6/2009 | Khosla et al. |

(Continued)

FOREIGN PATENT DOCUMENTS

AU 2003277989 B2 6/2004
CA 1299099 C 4/1992

(Continued)

OTHER PUBLICATIONS

Ontiveros et al. ("A whole blood cytokine release assay employing short-term gluten challenge identifies patients with celiac disease on a gluten free diet" available Jun. 15, 2012).*
Bakshi et al. (Gastroenterol Hepatol (NY) Sep. 2012; 8(9): 582-588).*
International Search Report and Written Opinion for Application No. PCT/US2014/054959 dated Dec. 3, 2014.
International Preliminary Report on Patentability dated Mar. 24, 2016 for Application No. PCT/US2014/054959.
[No Author Listed] Safety and tolerability of Nexvax2 in subjects with celiac disease. Clinical Trial Identifier NCT02528799. ImmusanT, Inc. Clinicaltrials.gov. Aug. 17, 2015. Retrieved online via https://clinicaltrials.gov/ct2/show/NCT02528799?term=NexVax2&rank=1. 4 pages.

(Continued)

Primary Examiner — James H Alstrum-Acevedo
Assistant Examiner — Tara L Martinez
(74) Attorney, Agent, or Firm — Wolf, Greenfield & Sacks, P.C.

(57) ABSTRACT

Provided herein are methods and compositions for treating subjects with Celiac disease.

21 Claims, 19 Drawing Sheets
Specification includes a Sequence Listing.

(56) References Cited

U.S. PATENT DOCUMENTS

| | | |
|---|---|---|
| 2009/0226471 A1 | 9/2009 | Kwok et al. |
| 2009/0269285 A1 | 10/2009 | Anderson et al. |
| 2010/0221712 A1 | 9/2010 | Radford et al. |
| 2011/0293644 A1 | 12/2011 | Anderson et al. |
| 2011/0311536 A1 | 12/2011 | von Boehmer et al. |
| 2012/0083004 A1 | 4/2012 | Khosla et al. |
| 2012/0107847 A1 | 5/2012 | Bruins et al. |
| 2013/0058970 A1 | 3/2013 | Kishimoto et al. |
| 2013/0078267 A1 | 3/2013 | Anderson et al. |
| 2015/0050303 A1 | 2/2015 | Anderson et al. |
| 2015/0320887 A1 | 11/2015 | Fondazione et al. |
| 2016/0041148 A1 | 2/2016 | Anderson et al. |
| 2016/0238590 A1 | 3/2016 | Anderson et al. |
| 2017/0042991 A1 | 2/2017 | Anderson et al. |
| 2017/0045513 A1 | 2/2017 | Anderson et al. |
| 2017/0045529 A1 | 2/2017 | Anderson et al. |
| 2017/0059582 A1 | 3/2017 | Anderson et al. |
| 2017/0097346 A1 | 4/2017 | Anderson et al. |
| 2017/0158743 A1 | 6/2017 | Anderson et al. |
| 2017/0218453 A1 | 8/2017 | Anderson et al. |
| 2017/0232083 A1 | 8/2017 | Anderson et al. |

FOREIGN PATENT DOCUMENTS

| | | |
|---|---|---|
| CN | 1703505 A | 11/2005 |
| EP | 0 296 158 B1 | 6/1992 |
| EP | 0905518 A1 | 3/1999 |
| EP | 1 332 760 A1 | 8/2003 |
| EP | 1 453 539 B1 | 9/2004 |
| EP | 1 393 070 B1 | 8/2007 |
| EP | 1 561 106 B1 | 4/2009 |
| EP | 1 740 949 B1 | 11/2011 |
| EP | 2 409 711 A1 | 1/2012 |
| EP | 2762487 A1 | 8/2014 |
| IT | 2007FE003 | 2/2007 |
| JP | 2003-511670 A | 3/2003 |
| JP | 2006-512893 A | 4/2006 |
| JP | 2008-508856 A | 3/2008 |
| JP | 4932112 B2 | 5/2012 |
| JP | 5635302 B2 | 12/2014 |
| WO | WO 93/19178 A2 | 9/1993 |
| WO | WO 96/06630 A1 | 3/1996 |
| WO | WO 96/07428 A1 | 3/1996 |
| WO | WO 2001/25793 A2 | 4/2001 |
| WO | WO 2002/083722 A2 | 10/2002 |
| WO | WO 2003/066079 A2 | 8/2003 |
| WO | WO 2003/096979 A2 | 11/2003 |
| WO | WO 2003/096984 A2 | 11/2003 |
| WO | WO 2003/104273 A2 | 12/2003 |
| WO | WO 2004/042396 A1 | 5/2004 |
| WO | WO 2004/045392 A2 | 6/2004 |
| WO | WO 2005/105129 A2 | 11/2005 |
| WO | WO 2007/019411 A2 | 2/2007 |
| WO | WO 2007/022477 A2 | 2/2007 |
| WO | WO 2007/047303 A2 | 4/2007 |
| WO | WO 2008/028489 | 3/2008 |
| WO | WO 2008/052185 | 5/2008 |
| WO | WO 2008/090223 A2 | 7/2008 |
| WO | WO 2008/113119 A1 | 9/2008 |
| WO | WO 2009/131909 A2 | 10/2009 |
| WO | WO 2009/139887 A2 | 11/2009 |
| WO | WO 2010/009494 A1 | 1/2010 |
| WO | WO 2010/060155 A1 | 6/2010 |
| WO | WO 2011/000773 A1 | 1/2011 |
| WO | WO 2011/075773 A1 | 6/2011 |
| WO | WO 2011/146968 A1 | 12/2011 |
| WO | WO 2013/000021 A1 | 1/2013 |
| WO | WO 2013/016427 A1 | 1/2013 |
| WO | WO 2013/085851 A2 | 6/2013 |
| WO | WO 2014/152233 A1 | 9/2014 |
| WO | WO 2015/038624 A1 | 3/2015 |
| WO | WO 2015/041680 A1 | 3/2015 |
| WO | WO 2015/164714 A1 | 10/2015 |
| WO | WO 2015/164717 A1 | 10/2015 |
| WO | WO 2015/164721 A1 | 10/2015 |
| WO | WO 2015/164722 A1 | 10/2015 |
| WO | WO 2015/164727 A1 | 10/2015 |
| WO | WO 2015/164747 A1 | 10/2015 |
| WO | WO 2015/164752 A1 | 10/2015 |
| WO | WO 2016/054038 A1 | 4/2016 |

OTHER PUBLICATIONS

[No Author Listed] Safety study of Nexvax2 in subjects with coeliac disease. Clinical Trial Identifier NCT00879749. Nexpep Pty Ltd. Clinicaltrials.gov. Apr. 5, 2011. Retrieved online via https://clinicaltrials.gov/ct2/show/NCT00879749?term=NexVax2&rank=2. 3 pages.

[No Author Listed], Biosis Chem Abstracts Database. Accession No. PREV201100403721. 2005. Gregor et al., Gastroenterol. May 2011;5(1):S437-8. Abstract.

[No Author Listed], Diagnosis and treatment of coeliac disease targeting gluten-specific T cells. Presentation. Burnet Institute. Melbourne, Australia. May 29, 2011. 48 pages.

[No Author Listed], ImmusanT Initiates Clinical Trials of Nexvax2 Therapeutic Vaccine for Celiac Disease. ImmusanT Press Release. Cambridge, MA. Sep. 4, 2012. 2 pgs.

[No Author Listed], ImmusanT Names Patrick Griffin as Chief Medical Officer, Expands Management Team. ImmusanT Press Release. Cambridge, MA. Mar. 19, 2012. 2 pgs.

[No Author Listed], ImmusanT Raises $20 Million in Series A Financing to Advance Immunotherapeutic and Diagnostic for Celiac Disease. ImmusanT Press Release. Cambridge, MA. Dec. 13, 2011. 2 pgs.

[No Author Listed], ImmusanT Reports Positive Results from Nexvax2 Phase 1 Study in Celiac Disease: Data Featured in Poster of Distinction and Symposia on Advances in Celiac Disease at Digestive Disease Week. Chicago, Illinois, May 9, 2011. 3 pgs.

[No Author Listed], Link Between Gluten and Immune Reaction Revealed for HLA DQ8 Celiac Disease. ImmusanT Press Release. Cambridge, MA. Oct. 11, 2012. 2 pgs.

[No Author Listed], Start-Up ImmunsanT Seeks to Restore Tolerance to Gluten in Celiac Disease with Immunotherapy. PR Newswire. Mar. 3, 2011. Last Accessed on Nov. 13, 2012 from http://www.prnewswire.com/news-releases/start-up-immusant-seeks-to-restore-tolerance-to-gluten-in-celiac-disease-with-immunotherapy-117996359.html.

[No Author Listed], Vaccination for celiac disease: utopia or concrete hope for celiac disease recovery. AIC Presentation. Florence, Italy. Mar. 30, 2012. 23 pages.

[No Author Listed], WPI Database Submission, Accession No. AED68481; Shan et al..; Jan. 12, 2006. 2 pages.

Anderson et al., Acrocyanosis due to imipramine. Arch Dis Child. Feb. 1988;63(2):204-5.

Anderson et al., Antagonists and non-toxic variants of the dominant wheat gliadin T cell epitope in coeliac disease. Gut. Apr. 2006;55(4):485-91. Epub Nov. 18, 2005.

Anderson et al., Bioactivity of peptides homologous to the coeliac disease-specific dominant A-gliadin T cell epitope. 2001. Abstract 3694.

Anderson et al., Bioactivity of peptides homologous to the coeliac disease-specific dominant T-cell epitope. British Soc Gast Poster. 2001. 1 page.

Anderson et al., Bioactivity of peptides homologous to the coeliac disease-specific dominant T-cell epitope. DDW Poster. 2001. 1 page.

Anderson et al., Celiac disease associated with HLA-DQ8 and DQ2 have different T-cell repertoires in vivo. 2003. Abstract 130.

Anderson et al., Celiac Disease. Chapter 22 in Evidence-Based Gastroenterology. Eds Irvine et al. 2000. BC Decker Inc. Ontario, Canada. pp. 307-322.

Anderson et al., Coeliac disease. Check Program of Self Assessment. 2005. The Royal Australian College of General Practitioners. Victoria, Australia. pp. 1-32.

Anderson et al., Definitive T cell epitope mapping for a human disease: gluten challenge in coeliac disease identifies a dominant transglutaminase-deamidated T cell epitope. 2001 Kiel Conference Proceedings. 13 pgs.

(56) References Cited

OTHER PUBLICATIONS

Anderson et al., In vivo antigen challenge in celiac disease identifies a single transglutaminase-modified peptide as the dominant A-gliadin T-cell epitope. Nat Med. Mar. 2000;6(3):337-42.
Anderson et al., In vivo cross-reactivity of wheat and rye T-cell epitopes in celiac disease. AGA Abstracts 2003. Abstract W1364.
Anderson et al., Peripheral blood T cells induced by gluten challenge in coeliac disease target a specific molecular motif and express a gut-homing integrin. 2001 Abstract 3695.
Anderson et al., Peripheral blood T cells induced by gluten challenge in coeliac disease target a specific motif and express a gut-homing integrin. DDW Poster. 2001. 1 page.
Anderson et al., Screening for coeliac disease: integration of technology and stakeholders. eliA™J. 2004;1:1-11.
Anderson et al., T cells in peripheral blood after gluten challenge in coeliac disease. Gut. Sep. 2005;54(9):1217-23.
Anderson et al., Vaccine against autoimmune disease: antigen-specific immunotherapy. Curr Opin Immunol. Jun. 2013;25(3):410-7. doi: 10.1016/j.coi.2013.02.004. Epub Mar. 13, 2013.
Anderson, Translating discovery of toxic gluten peptides to a peptide immunotherapy for coeliac disease. Presentation given in Wellington, New Zealand. 2010. 77 pages.
Anderson, A blueprint for the future of coeliac disease. Presentation for NZ Coeliac Society. 2011. 37 pages.
Anderson, A phase I study to determine safety, tolerability and bioactivity of Nexvax2® in HLA DQ2+ volunteers with celiac disease following long-term, strict gluten-free diet. Presentation. Kiama NSW. 2011. 15 pages.
Anderson, Coeliac disease in a select population: optimizing sero-genetic testing. Presentation. The George Institute. Sydney, Australia. 2010. 43 pages.
Anderson, Coeliac disease. Aust Fam Physician. Apr. 2005;34(4):239-42.
Anderson, Coeliac Disease: Diagnosis without biopsy, and therapy without dietary changes. Swiss Coeliac Day Presentation. Zurich, Switzerland. 2011. 53 pages.
Anderson, Coeliac T cell epitopes in cereals: What are they and why do they matter? AOECS Presentation. Helsinki, Finland. Sep. 6, 2012. 26 pages.
Anderson, Future Therapies. University Chicago Presentation. 2011. 60 pages.
Anderson, Genetic susceptibility and regulation of the immune response in celiac disease. DDW Presentation. 2011. 30 pages.
Anderson, Harnessing gluten toxicity to make a drug for coeliac disease. Presentation for The Garvan Institute. Sydney, Australia. 2010. 38 pages.
Anderson, Overcoming gluten toxicity: additions or replacements to diet? ICDS Presentation. Oslo, Norway. Jun. 22, 2011. 49 pages.
Anderson, Sunrise Session: Basic science celiac disease. DDW Presentation. 2011. 29 pages.
Anderson. Coeliac disease is on the rise. Med J Aust. Mar. 21, 2011;194(6):278-9.
Anderson. Coeliac disease: current approach and future prospects. Intern Med J. Oct. 2008;38(10):790-9.
Anderson. Coeliac disease: new tests, new genes and rising prevalence. MedicineToday. Jun. 2011;12(6):69-71.
Anderson. Development of a vaccine for celiac disease. Frontiers in Celiac Disease. 2008;12:172-180.
Anderson., Update in coeliac disease: from food to molecular therapeutics and diagnostics. ASCIA Presentation. 2011. 46 pages.
Arentz-Hansen et al., The intestinal T cell response to alpha-gliadin in adult celiac disease is focused on a single deamidated glutamine targeted by tissue transglutaminase. J Exp Med. Feb. 21, 2000;191(4):603-12.
Arentz-Hansen et al., Celiac lesion T cells recognize epitopes that cluster in regions of gliadins rich in proline residues. Gastroenterology. Sep. 2002;123(3):803-9.
Arentz-Hansen et al., The molecular basis for oat intolerance in patients with celiac disease. PLoS Med. Oct. 2004;1(1):e1. Epub Oct. 19, 2004.
Attwood, Genomics. The Babel of bioinformatics. Science. Oct. 20, 2000;290(5491):471-3. 5 pages.
Avalos et al., Monovalent engagement of the BCR activates ovalbumin-specific transnuclear B cells. J Exp Med. 2014;211(2):365-79.
Bakshi et al., Emerging therapeutic options for celiac disease: potential alternatives to a gluten-free diet. Gastroenterol Hepatol (N Y). Sep. 2012;8(9):582-8.
Bateman et al., IgA antibodies of coeliac disease patients recognise a dominant T cell epitope of A-gliadin. Gut. Sep. 2004;53(9):1274-8.
Beissbarth et al., A systematic approach for comprehensive T-cell epitope discovery using peptide libraries.Bioinformatics. Jun. 2005;21 Suppl 1:i29-37.
Biagi et al., A non-toxic analogue of a coeliac-activating gliadin peptide: a basis for immunomodulation? Aliment Pharmacol Ther. Jul. 1999;13(7):945-50.
Bodd et al., T-cell response to gluten in patients with HLA-DQ2.2 reveals requirement of peptide-MHC stability in celiac disease. Gastroenterology. Mar. 2012;142(3):552-61. doi: 10.1053/j.gastro.2011.11.021. Epub Nov. 19, 2011.
Bragde et al., Potential blood-based markers of celiac disease. BMC Gastroenterol. Oct. 9, 2014;14:176. doi: 10.1186/1471-230X-14-176.
Brottveit et al., Absence of somatization in non-coeliac gluten sensitivity. Scand J Gastroenterol. Jul. 2012;47(7):770-7.
Brottveit et al., Assessing possible celiac disease by an HLA-DQ2-gliadin Tetramer Test. Am J Gastroenterol. Jul. 2011;106(7):1318-24. doi: 10.1038/ajg.2011.23. Epub Mar. 1, 2011. Erratum in: Am J Gastroenterol. Apr. 2012;107(4):638.
Brottveit et al., Mucosal cytokine response after short-term gluten challenge in celiac disease and non-celiac gluten sensitivity. Am J Gastroenterol. May 2013;108(5):842-50. doi: 10.1038/ajg.2013.91. Epub Apr. 16, 2013.
Brottveit, Gluten challenge in coeliac disease and non-coeliac gluten sensitivity. Oslo University Hospital. 2012:2-74.
Broughton et al., Biased T Cell Receptor Usage Directed against Human Leukocyte Antigen DQ8-Restricted Gliadin Peptides Is Associated with Celiac Disease. Immunity. Oct. 19, 2012;37(4):611-21. Epub Oct. 11, 2012.
Brown et al., A phase I study to determine safety, tolerability and bioactivity of nexvax2 in HLA DQ2+ volunteers with celiac disease following a long-term, strict gluten free diet . AGA Abstracts. 2011; p. S-437-8: Abstract Sul235.
Brown et al., A phase I study to determine safety, tolerability and bioactivity of Nexvax2® in HLA DQ2+ volunteers with celiac disease following long-term, strict gluten-free diet. DDW Presentation. 2011. 6 pages.
Brown et al., A phase I study to determine safety, tolerability and bioactivity of Nexvax2® in HLA DQ2+ volunteers with celiac disease following long-term, strict gluten-free diet. DDW Poster. 2011. 1 page.
Brown et al., A phase I study to determine safety, tolerability and bioactivity of Nexvax2® in HLA DQ2+ volunteers with celiac disease following a long-term, strict gluten-free diet. Gastroenterology. May 2011;140(5):Suppl1:S437-8. Biosis Abstract Accession No. PREV201100403721.
Burton et al. Sequential transcriptional changes dictate safe and effective antigen-specific immunotherapy. Nat Commun. Sep. 3, 2014;5:4741. doi: 10.1038/ncomms5741.
Camarca et al., Short wheat challenge is a reproducible in-vivo assay to detect immune response to gluten. Clin Exp Immunol. Aug. 2012;169(2):129-36.
Camarca et al., Intestinal T cell responses to gluten peptides are largely heterogeneous: implications for a peptide-based therapy in celiac disease. J Immunol. Apr. 1, 2009;182(7):4158-66.
Camarca et al., Intestinal T-cell responses to gluten-derived peptides reveal a large repertoire and a hierarchy of gluten epitopes in adult HLA-DQ2-positive celiac patients. AGA Abstracts. 2006; p. A-94: Abstract 657.
Campbell et al., Peptide immunotherapy in allergic asthma generates IL-10-dependent immunological tolerance associated with linked epitope suppression. J Exp Med. Jul. 6, 2009;206(7):1535-47. doi: 10.1084/jem.20082901. Epub Jun. 15, 2009.

(56) References Cited

OTHER PUBLICATIONS

Catassi et al. (eds), Primary Prevention for Coeliac Disease the Utopia of the New Millennium? vol. I: Perspectives on Coeliac Disease. Proceedings of the Meeting on Coeliac Disease held in Pavia on Oct. 12, 2001. Published in 2003. AIC Press. Italian Coeliac Society. Pisa, Italy. pp. 1-112.

Catassi et al., A prospective, double-blind, placebo-controlled trial to establish a safe gluten threshold for patients with celiac disease. Am J Clin Nutr. Jan. 2007;85(1):160-6.

Catassi et al., World Perspective on Celiac Disease. J Pediatr Gastroenterol Nutr. Nov. 2012;55(5):494-499.

Cheng et al., CD4+, but not CD8+, T cells from mammary tumor-bearing mice have a down-regulated production of IFN-gamma: role of phosphatidyl serine. J Immunol. Mar. 15, 1998;160(6):2735-41.

Chowers et al., Increased proinflammatory cytokine gene expression in the colonic mucosa of coeliac disease patients in the early period after gluten challenge. Clin Exp Immunol. Jan. 1997;107(1):141-7.

Cornell et al., Characterization of the gliadin-derived peptides which are biologically active in coeliac disease. Clin Chim Acta. Dec. 31, 1992;213(1-3):37-50.

Cornell et al., In vitro mucosal digestion of synthetic gliadin-derived peptides in celiac disease. J Protein Chem. Jul. 1995;14(5):335-9.

Cornell et al., Studies of in vitro gamma-interferon production in coeliac disease as a response to gliadin peptides. Biochim Biophys Acta. May 25, 1994;1226(2):126-30. Abstract only.

Costa et al., A population study to optimize the role of serology and genetics in the diagnosis of celiac disease (CD). DDW Poster. 2011. 1 page.

Costa et al., A population study to optimize the role of serology and genetics in the diagnosis of celiac disease . AGA Abstracts. 2011; p. S-440: Abstract Su1246.

Costa et al., Quantifying community need and potential impact of rational testing for Coeliac Disease: A basis for disciplinary guidelines in Australia. Presentation. St. Georges, Sydney, Australia. 2011. 34 pages.

Daveson et al., Small bowel endoscopy and coeliac disease. Best Pract Res Clin Gastroenterol. Jun. 2012;26(3):315-23.

Daveson et al., Effect of hookworm infection on wheat challenge in celiac disease—a randomised double-blinded placebo controlled trial. PLoS One. Mar. 8, 2011;6(3):1-9.

De Kauwe et al., Resistance to celiac disease in humanized HLA-DR3-DQ2-transgenic mice expressing specific anti-gliadin CD4+ T cells. J Immunol. Jun. 15, 2009;182(12):7440-50. Doi: 10.4049/jimmunol.0900233.

Dioszeghy et al., Epicutaneous immunotherapy results in rapid allergen uptake by dendritic cells through intact skin and downregulates the allergen-specific response in sensitized mice. J Immunol. May 15, 2011;186(10):5629-37. doi: 10.4049/jimmunol.1003134. Epub Apr. 13, 2011.

Dioszeghy et al., The regulatory T cells induction by epicutaneous immunotherapy is sustained and mediates long-term protection from eosinophilic disorders in peanut-sensitized mice. Clin Exp Allergy. Jun. 2014;44(6):867-81. doi: 10.1111/cea.12312.

Erickson, 10 Promising Therapeutic Vaccines. Fierce Vaccines. Oct. 27, 2011. Last Accessed on Nov. 13, 2012 from http://www.fiercevaccines.com/story/10-promising-therapeutic-vaccines/2011-10-27.

Fellrath et al., Allergen-specific T-cell tolerance induction with allergen-derived long synthetic peptides: results of a phase I trial. J Allergy Clin Immunol. Apr. 2003;111(4):854-61.

Fleckenstein et al., Gliadin T cell epitope selection by tissue transglutaminase in celiac disease. Role of enzyme specificity and pH influence on the transamidation versus deamidation process. J Biol Chem. Sep. 13, 2002;277(37):34109-16. Epub Jul. 1, 2002.

Fornari et al., Pre- and post-treatment serum levels of cytokines IL-lbeta, IL-6, and IL-1 receptor antagonist in celiac disease. Are they related to the associated osteopenia? Am J Gastroenterol. Mar. 1998;93(3):413-8.

Forster, Interferon signatures in immune disorders and disease. Immunol Cell Biol. May 2012;90(5):520-7.

Fraser et al., Coeliac disease: in vivo toxicity of the putative immunodominant epitope. Gut. Dec. 2003;52(12):1698-702.

GENBANK Submission; NIH/NCBI, Accession No. AAB28161;Sainova et al.; Jan. 19, 1994. 1 page.

GENBANK Submission; NIH/NCBI, Accession No. AAZ76368.1; Han et al.; Mar. 20, 2008.. 1 page.

GENBANK Submission; NIH/NCBI, Accession No. ABS72146; Chen et al.; Aug. 5, 2007. 1 page.

Goldman, Best thing since sliced bread? a (potential) new diagnostic for celiac disease. Scope. Stanford Medicine. Jun. 22, 2013. http://scopeblog.stanford.edu/2013/07/22/best-thing-since-sliced-bread-a-potential-new-diagnostic-for-celiac-disease/ [last accessed Nov. 19, 2013].

Hagan, The vaccine that means coeliacs can eat wheat. Good Health. Tuesday, Oct. 9, 2012. 1 pg.

Haines et al., Systematic review: The evidence base for long-term management of coeliac disease. Aliment Pharmacol Ther. Nov. 1, 2008;28(9):1042-66. Epub Jul. 30, 2008.

Hall et al., Precise probes of type II interferon activity define the origin of interferon signatures in target tissues in rheumatic diseases. Proc Natl Acad Sci U S A. Oct. 23, 2012;109(43):17609-14.

Han et al., Dietary gluten triggers concomitant activation of CD4+ and CD8+ αβ T cells and γδ T cells in celiac disease. Proc Natl Acad Sci U S A. Aug. 6, 2013;110(32):13073-8.

Hardy et al., Ingestion of oats and barley in patients with celiac disease mobilizes cross-reactive T cells activated by avenin peptides and immuno-dominant hordein peptides, Journal of Autoimmunity (2014), http://dx.doi.org/10.1016/j.jaut.2014.10.003. Article in press.

Henderson et al., A structural and immunological basis for the role of human leukocyte antigen DQ8 in celiac disease. Immunity. Jul. 2007;27:23. doi:10.1016/j.immuni.2007.05.015. 12 pages.

Henderson et al., Supplemental Data: A structural and immunological basis for the role of human leukocyte antigen DQ8 in celiac disease. Immunity. Jul. 2007;27:1-9.

Henderson et al., The production and crystallization of the human leukocyte antigen class II molecules HLA-DQ2 and HLA-DQ8 complexed with deamidated gliadin peptides implicated in coeliac disease. Acta Crystallogr Sect F Struct Biol Cryst Commun. Dec. 1, 2007;63(Pt 12):1021-5. Epub Nov. 21, 2007.

Hirahara et al., New specific immunotherapies for Japanese cedar pollinosis. Biolog Eng. 2002;80(4): 152-55.

Hoyne et al., Regulation of house dust mite responses by intranasally administered peptide: transient activation of CD4+ T cells precedes the development of tolerance in vivo. Int Immunol. Mar. 1996;8(3):335-42.

Huan et al., Single-chain recombinant HLA-DQ2.5/peptide molecules block α2-gliadin-specific pathogenic CD4+ T-cell proliferation and attenuate production of inflammatory cytokines: a potential therapy for celiac disease. Mucosal Immunol. Jan. 2011;4(1):112-20. Epub Aug. 25, 2010.

Keech et al., Immune tolerance induced by peptide immunotherapy in an HLA DQ2-dependent mouse model of gluten immunity. Gastroenterology May 2009;136(5):A57. Abstract 355.

Kooy-Winkelaar et al., Gluten-specific T cells cross-react between HLA-DQ8 and the HLA-DQ2α/DQ8β transdimer. J Immunol. Nov. 15, 2011;187(10):5123-9. doi: 10.4049/jimmunol.1101179. Epub Oct. 17, 2011.

Maguire et al., The safety and efficacy of ALLERVAX CAT in cat allergic patients. Clin Immunol. Dec. 1999;93(3):222-31.

Marylia et al., A population study to optimize the role of serology and genetics in the diagnosis of celiac disease (CD). DDW Poster. 2011. 1 page.

McAllister et al., The immunopathogenesis of celiac disease reveals possible therapies beyond the gluten-free diet. Semin Immunopathol. Jul. 2012;34(4):581-600. doi: 10.1007/s00281012-0318-8. Epub Jun. 7, 2012.

(56) References Cited

OTHER PUBLICATIONS

McSorley et al., Suppression of inflammatory immune responses in celiac disease by experimental hookworm infection. PLoS One. 2011;6(9):1-7. Epub Sep. 16, 2011.

Molberg et al., Tissue transglutaminase selectively modifies gliadin peptides that are recognized by gut-derived T cells in celiac disease. Nat Med. Jun. 1998;4(6):713-7.

Molberg et al., T cells from celiac disease lesions recognize gliadin epitopes deamidated in situ by endogenous tissue transglutaminase. Eur J Immunol. May 2001;31(5):1317-23.

Mondoulet et al., Epicutaneous immunotherapy (EPIT) blocks the allergic esophago-gastro-enteropathy induced by sustained oral exposure to peanuts in sensitized mice. PLoS One. 2012;7(2):e31967. doi: 10.1371/journal.pone.0031967. Epub Feb. 21, 2012.

Mondoulet et al., Intact skin and not stripped skin is crucial for the safety and efficacy of peanut epicutaneous immunotherapy (EPIT) in mice. Clin Transl Allergy. Nov. 12, 2012;2(1):22. doi: 10.1186/2045-7022-2-22.

Mondoulet et al.,. Specific epicutaneous immunotherapy prevents sensitization to new allergens in a murine model. J Allergy Clin Immunol. Jun. 2015;135(6):1546-57.e4. doi: 10.1016/j.jaci.2014.11.028. Epub Jan. 9, 2015.

Müller et al., Successful immunotherapy with T-cell epitope peptides of bee venom phospholipase A2 induces specific T-cell anergy in patients allergic to bee venom. J Allergy Clin Immunol. Jun. 1998;101(6 Pt 1):747-54.

Ngo et al., Computational Complexity, Protein Structure Prediction, and the Levinthal Paradox. The Protein Folding Problem and tertiary Structure Prediction. Merz et al., Eds. 1994:14,492-5.

Norman et al., Treatment of cat allergy with T-cell reactive peptides. Am J Respir Crit Care Med. Dec. 1996;154(6 Pt 1):1623-8.

Oberhuber et al., The histopathology of coeliac disease: time for a standardized report scheme for pathologists. Eur J Gastroenterol Hepatol. Oct. 1999;11(10):1185-94. Review.

Oldfield et al., Effect of T-cell peptides derived from Fel d 1 on allergic reactions and cytokine production in patients sensitive to cats: a randomised controlled trial. Lancet. Jul. 6, 2002;360(9326):47-53.

Ontiveros et al., A whole blood cytokine release assay employing short-term gluten challenge identifies patients with celiac disease on a gluten free diet . AGA Abstracts. 2012; p. S-271: Abstract Sa1317.

Ontiveros et al., A whole blood cytokine release assay employing short-term gluten challenge identifies patients with celiac disease on a gluten free diet. DDW ePoster. And Poster. 2012. 1 page.

Ontiveros et al., A whole blood cytokine release assay employing short-term gluten challenge identifies patients with celiac disease on a gluten free diet. DDW ePoster. And Poster. 2012. 9 pages.

Ontiveros et al., Ex-vivo whole blood secretion of interferon (IFN)-γ and IFN-γ-inducible protein-10 measured by enzyme-linked immunosorbent assay are as sensitive as IFN-γ enzyme-linked immunospot for the detection of gluten-reactive T cells in human leucocyte antigen (HLA)-DQ2.5(+)-associated coeliac disease. Clin Exp Immunol. Feb. 2014;175(2):305-15. doi: 10.1111/cei.12232.

Osman et al., B cell epitopes of gliadin. Clin Exp Immunol. Aug. 2000;121(2):248-54.

Paterson et al., The safety, tolerance, pharmacokinetic and pharmacodynamic effects of single doses of AT-1001 in coeliac disease subjects: a proof of concept study. Aliment Pharmacol Ther. Sep. 1, 2007;26(5):757-66.

Pincus, Coeliac vaccine trials world first. 12 Weekend Professional Health. The Weekend Australian. Mar. 21-22, 2009. 1 page.

Potkin et al., Wheat gluten challenge in schizophrenic patients. Am J Psychiatry. Sep. 1981;138(9):1208-11.

Przemioslo et al., Raised pro-inflammatory cytokines interleukin 6 and tumour necrosis factor alpha in coeliac disease mucosa detected by immunohistochemistry. Gut. Oct. 1994;35(10):1398-403.

Qiao et al., Refining the rules of gliadin T cell epitope binding to the disease-associated DQ2 molecule in celiac disease: importance of proline spacing and glutamine deamidation. J Immunol. Jul. 1, 2005;175(1):254-61.

Quarsten et al., Staining of celiac disease-relevant T cells by peptide-DQ2 multimers. J Immunol. Nov. 1, 2001;167(9):4861-8.

Raki et al., Tetramer visualization of gut-homing gluten-specific T cells in the peripheral blood of celiac disease patients. Proc Natl Acad Sci U S A. Feb. 20, 2007;104(8):2831-6. Epub Feb. 16, 2007.

Rönnblom et al., The interferon signature in autoimmune diseases. Curr Opin Rheumatol. Mar. 2013;25(2):248-53.

Rossi et al., Intravenous or intranasal administration of gliadin is able to down-regulate the specific immune response in mice. Scand J Immunol. Aug. 1999;50(2):177-82.

Rubio-Tapia et al., ACG clinical guidelines: diagnosis and management of celiac disease. Am J Gastroenterol. May 2013;108(5):656-76.

Saito, New Immunotherapy—Peptide therapy & DNA vaccine therapy. Clinical of Allergy. Nov. 2003; 23(12):26-30.

Saxby et al., A study of IgA antibodies to a T cell epitope of α-gliadin in coeliac disease. British Soc Immunol Poster. 2002. 1 page.

Scibilia et al., Wheat allergy: a double-blind, placebo-controlled study in adults. J Allergy Clin Immunol. Feb. 2006;117(2):433-9.

Shan et al., Identification and analysis of multivalent proteolytically resistant peptides from gluten: implications for celiac sprue. J Proteome Res. Sep.-Oct. 2005;4(5):1732-41.

Sjöstrom et al., Identification of a gliadin T-cell epitope in coeliac disease: general importance of gliadin deamidation for intestinal T-cell recognition. Scand J Immunol. Aug. 1998;48(2):111-5.

Skerritt et al., Antigenecity of wheat prloamins: detailed epitope analysis using a panel of monoclonal antibodies. J Cereal Sci. 2000;32:259-79.

Skolnick et al., From genes to protein structure and function: novel applications of computational approaches in the genomic era. Trends Biotechnol. Jan. 2000;18(1):34-9.

Sollid et al., Nomenclature and listing of celiac disease relevant gluten T-cell epitopes restricted by HLA-DQ molecules. Immunogenetics. Jun. 2012;64(6):455-60. doi: 10.1007/s00251-012-0599-z. Epub Feb. 10, 2012.

Stewart et al., Dominance, hierarchy and redundancy of T cell stimulatory peptides in celiac disease. AGA Abstracts. 2009; p. A-57: Abstract 354.

Tan et al., Non-axial bone fracture but not depression as a risk factor for coeliac disease. Intern Med J. Mar. 2010;40(3):225-7.

Tanner et al., Dissecting the T-cell response to hordeins in coeliac disease can develop barley with reduced immunotoxicity. Aliment Pharmacol Ther. Nov. 2010;32(9):1184-91. Epub Sep. 15, 2010.

Tarlac et al., HLA-DR3-DQ2 Mice Do Not Develop Ataxia in the Presence of High Titre Anti-gliadin Antibodies. Cerebellum. Oct. 20, 2012.

Tjon et al., Celiac disease: how complicated can it get? Immunogenetics. Oct. 2010;62(10):641-51. doi: 10.1007/s00251-010-0465-9. Epub Jul. 27, 2010. Review.

Tollefsen et al., HLA-DQ2 and -DQ8 signatures of gluten T cell epitopes in celiac disease. J Clin Invest. Aug. 2006;116(8):2226-36.

Tye-Din et al., A 35mer peptide with T cell stimulatory activity comparable to whole gliadin: a lead compound for peptide immunotherapy in celiac disease. AGA Abstracts. 2006; p. A-95: Abstract 661.

Tye-Din et al., A comprehensive bioinformatic and functional screen of wheat gluten T-cell epitopes in HLA-DQ2 celiac disease in vivo. AGA Abstracts. 2005; p. A-2: Abstract 13.

Tye-Din et al., A third celiac disease: genotyping reveals a functionally distinct subtype. AGA Abstracts. 2006; p. A-664: Abstract W1238.

Tye-Din et al., Comprehensive T-cell epitope characterization in HLA-DQ8 celiac disease. AGA Abstracts. 2005; p. A-2: Abstract 14.

Tye-Din et al., Comprehensive, quantitative mapping of T cell epitopes in gluten in celiac disease. Sci Transl Med. Jul. 21, 2010;2(41):1-14.

(56) References Cited

OTHER PUBLICATIONS

Tye-Din et al., HLA-DQ genotype reverses incorrect diagnosis of celiac disease. AGA Abstracts. 2005; p. A-259: Abstract S1805.

Tye-Din et al., Immunopathogenesis of celiac disease. CurrGastroenterol Rep. Oct. 2008;10(5):458-65.

Tye-Din et al., Oats induce avenin specific T-cells in celiac disease. AGA Abstracts. 2005; p. A-259: Abstract S1804.

Tye-Din et al., Supplementary Materials for Comprehensive, quantitative mapping of T cell epitopes in gluten in celiac disease. Sci Transl Med. Jul. 21, 2010;2(41):41ra51.

Tye-Din et al., T-cell epitope hierarchy after rye and barley ingestion in celiac disease. AGA Abstracts. 2005; p. A-259: Abstract S1803.

Tye-Din et al., The effects of ALV003 pre-digestion of gluten on immune response and symptoms in celiac disease in vivo. Clin Immunol. Mar. 2009;134(3):1-7.

Tye-Din et al., Universal and grain-specific T cell epitopes in celiac disease. AGA Abstracts. 2007; p. A-108: Abstract 760.

Vader et al., Characterization of cereal toxicity for celiac disease patients based on protein homology in grains. Gastroenterology. Oct. 2003;125(4):1105-13.

Vader et al., Specificity of tissue transglutaminase explains cereal toxicity in celiac disease. J Exp Med. Mar. 4, 2002;195(5):643-9.

Vader et al., The gluten response in children with celiac disease is directed toward multiple gliadin and glutenin peptides. Gastroenterology. Jun. 2002;122(7):1729-37.

Van De Wal et al., Glutenin is involved in the gluten-driven mucosal T cell response. Eur J Immunol. Oct. 1999;29(10):3133-9.

Van De Wal et al., Selective deamidation by tissue transglutaminase strongly enhances gliadin-specific T cell reactivity. J Immunol. Aug. 15, 1998;161(4):1585-8.

Van De Wal et al., Small intestinal T cells of celiac disease patients recognize a natural pepsin fragment of gliadin. Proc Natl Acad Sci U S A. Aug. 18, 1998;95(17):10050-4.

Verginis et al., Induction of antigen-specific regulatory T cells in wild-type mice: visualization and targets of suppression. Proc Natl Acad Sci U S A. Mar. 4, 2008;105(9):3479-84. doi: 10.1073/pnas.0800149105. Epub Feb. 25, 2008.

Walker-Smith et al., Revised criteria for diagnosis of coeliac disease. Report of Working Group of European Society of Paediatric Gastroenterology and Nutrition. Arch Dis Child. Aug. 1990;65(8):909-11.

Xia et al., Inhibition of HLA-DQ2-mediated antigen presentation by analogues of a high affinity 33-residue peptide from alpha2-gliadin. J Am Chem Soc. Feb. 15, 2006;128(6):1859-67.

[No Author Listed], CXCL10 Mouse ELISA Kit, Catalog No. BMS6018. Aug. 17, 2008—date provided by Google®. Last Accessed on Apr. 10, 2018 from https://www.thermofisher.com/order/catalog/product/BMS6018.

[No Author Listed], IP-10 (Interferon Gamma-Induced Protein 10). Jun. 10, 2005—date provided by Google®. Last Accessed on Apr. 10, 2018 from https://pacbio.com/biomarker/assay-detail/226/.

Beck et al., Abstract W1370: Adherence to a gluten free diet is the main determinant of chemokine expression in celiac disease. Gastroenterol. Jan. 1, 2003;124(4):A657.

Björck et al., Serum cytokine pattern in young children with screening detected coeliac disease. Clin Exp Immunol. Feb. 2015;179(2):230-5. doi: 10.1111/cei.12454.

Camarca et al., Intestinal T-cell responses to gluten-derived peptides reveal a large repertoire and a hierarchy of gluten epitopes in adult HLA-DQ2-positive celiac patients. J Pediatric Gastroenterol Nutr. May 2006;42(5):E19.

Cataldo et al., Plasma cytokine profiles in patients with celiac disease and selective IgA deficiency. Pediatr Allergy Immunol. Aug. 2003;14(4):320-4.

Kilmartin et al., Abstract 2026: Immune responses to gliadin but not to avenin in organ culture studies of coeliac biopsies. Gastronenterol. Jan. 1, 2001:A396.

Lammi et al., Increased peripheral blood CD4+ T cell responses to deamidated but not to native gliadin in children with coeliac disease. Clin Exp Immunol. May 2012;168(2):207-14. doi: 10.1111/j.1365-2249.2012.04575.x.

Liu et al., Exploring T cell reactivity to gliadin in young children with newly diagnosed celiac disease. Autoimmune Dis. 2014;2014:927190. doi:10.1155/2014/927190. Epub Mar. 3, 2014.

Murray et al., HLA DQ Gene Dosage and Risk and Severity of Celiac Disease. Clin Gastroenterol Hepatol. Dec. 2007; 5(12):1406-1412.

Romaldini et al., Serum soluble interleukin-2 receptor, interleukin-6, and tumor necrosis factor-alpha levels in children with celiac disease: response to treatment. J Pediatr Gastroenterol Nutr. Oct. 2002;35(4):513-7.

Vives-Pi et al., Biomarkers for diagnosis and monitoring of celiac disease. J Clin Gastroenterol. Apr. 2013;47(4):308-13. doi: 10.1097/MCG.0b013e31827874e3. Review.

Barratt et al., Factors influencing the type, timing and severity of symptomatic responses to dietary gluten in patients with biopsy-proven coeliac disease. J Gastrointestin Liver Dis. Dec. 2013;22(4):391-6.

Blumenthal et al., "Definition of an Allergen." Allergens and Allergen Immunotherapy. Marcel Decker. "Lockey, Bukantz, and Bousquet." New York. 2004:37-50.

Friedl-Hajek et al., Identification of a highly promiscuous and an HLA allele-specific T-cell epitope in the birch major allergen Bet v 1: HLA restriction, epitope mapping and TCR sequence comparisons. Clin Exp Allergy. Apr. 1999;29(4):478-87.

Kinnunen et al., Potential of an altered peptide ligand of lipocalin allergen Bos d 2 for peptide immunotherapy. J Allergy Clin Immunol. Apr. 2007;119(4):965-72. Epub Mar. 1, 2007.

Schein et al., Bioinformatics approaches to classifying allergens and predicting cross-reactivity. Immunol Allergy Clin North Am. Feb. 2007;27(1):1-27.

Silvester et al., Symptomatic suspected gluten exposure is common among patients with coeliac disease on a gluten-free diet. Aliment Pharmacol Ther. Sep. 2016;44(6):612-9. doi: 10.1111/apt.13725. Epub Jul. 22, 2016.

\* cited by examiner

Ex Vivo Whole Blood Cytokine Release Stimulated by Immuno-dominant Gluten-derived T-cell Epitopes before and after Celiac Disease Patients are Treated

| Subject | Cohort | Dose peptide composition/µg | Doses | Pre-treatment | Post-treatment |
|---|---|---|---|---|---|
| A | 1 | 150 | 16 | R | NR |
| B | 1 | 150 | 16 | R | NR |
| C | 1 | 150 | 16 | R | R |
| D | 1 | 150 | 16 | R | NR |
| E | 1 | 150 | 15 | R | R |
| F | 1 | 150 | 16 | R | NR |
| G | 1 | 150 | 16 | NR | NR |
| H | 1 | 150 | 16 | R | NR |
| I | 2 | 300 | 16 | NR | NR |
| J | 2 | 300 | 16 | R | NR |
| K | 2 | 300 | 5 | R | NR |
| L | 2 | 300 | 4 | R | NR |
| M | 1 | 0 | 16 | R | R |
| N | 1 | 0 | 16 | R | NR |
| O | 1 | 0 | 16 | R | R |
| P | 1 | 0 | 15 | R | R |
| Q | 2 | 0 | 10 | R | NR |
| R | 2 | 0 | 16 | R | R |

R=reactive, NR= non-reactive in ex vivo whole blood peptide-stimulated cytokine release assay, where IFNγ levels in plasma after 24-incubation is measured to be greater than or equal to 7.2 pg/ml.

Fig. 5

| | | (Baseline) Week-1 | Week 1 | Week 2 | Week 3 | Week 4 | Week 5 | Week 6 | Week 7 | Week 8 |
|---|---|---|---|---|---|---|---|---|---|---|
| Cohort 1 150 mg (QC) | Number of Subjects | 8 | 8 | 8 | 8 | 8 | 8 | 8 | 8 | 8 |
| | Mean, Weekly Average | 1.073 | 1.533 | 1.271 | 1.125 | 1.09 | 1.073 | 1.264 | 1.087 | 1.139 |
| | Stdev, Weekly Average | 0.11 | 0.491 | 0.324 | 0.255 | 0.151 | 0.158 | 0.509 | 0.166 | 0.205 |
| | Median, Weekly Average | 1.056 | 1.333 | 1.153 | 1.042 | 1.042 | 1 | 1.069 | 1 | 1.042 |
| | Minimum, Weekly Average | 1 | 1 | 1 | 1 | 1 | 1 | 1 | 1 | 1 |
| | Maximum, Weekly Average | 1.333 | 2.417 | 1.944 | 1.75 | 1.444 | 1.444 | 2.5 | 1.472 | 1.542 |
| | Maximum Daily Score | 1.667 | 4.333 | 2.5 | 2.333 | 1.667 | 3.167 | 3.333 | 2.167 | 2.5 |
| | #Subjects with score>4 | 0 | 1 | 0 | 0 | 0 | 0 | 0 | 0 | 0 |
| | Mean days/subject with score>4 | 0 | 0.125 | 0 | 0 | 0 | 0 | 0 | 0 | 0 |
| | Max days/subject with score>4 | 0 | 1 | 0 | 0 | 0 | 0 | 0 | 0 | 0 |
| Cohort 2 300 mg (QC) | Number of Subjects | 10 | 10 | 9 | 6 | 4 | 3 | 2 | 2 | 3 |
| | Mean, Weekly Average | 1.222 | 1.719 | 1.493 | 1.187 | 1.331 | 1.278 | 1.014 | 1.028 | 1 |
| | Stdev, Weekly Average | 0.224 | 0.738 | 0.577 | 0.21 | 0.162 | 0.217 | 0.02 | 0.039 | 0 |
| | Median, Weekly Average | 1.25 | 1.556 | 1.361 | 1.153 | 1.389 | 1.389 | 1.014 | 1.028 | 1 |
| | Minimum, Weekly Average | 1 | 1 | 1 | 1 | 1.1 | 1.028 | 1 | 1 | 1 |
| | Maximum, Weekly Average | 1.667 | 3.472 | 2.528 | 1.444 | 1.444 | 1.417 | 1.028 | 1.056 | 1 |
| | Maximum Daily Score | 2.167 | 4.667 | 2.833 | 1.667 | 3.667 | 2.667 | 1.167 | 1.333 | 1 |
| | #Subjects with score>4 | 0 | 1 | 0 | 0 | 0 | 0 | 0 | 0 | 0 |
| | Mean days/subject with score>4 | 0 | 0.1 | 0 | 0 | 0 | 0 | 0 | 0 | 0 |
| | Max days/subject with score>4 | 0 | 1 | 0 | 0 | 0 | 0 | 0 | 0 | 0 |
| Cohort 7 150 mg (Biopsy) | Number of Subjects | 7 | 7 | 7 | 7 | 7 | 7 | 7 | 7 | 7 |
| | Mean, Weekly Average | 1.155 | 1.329 | 1.115 | 1.067 | 1.159 | 1.079 | 1.123 | 1.108 | 1.095 |
| | Stdev, Weekly Average | 0.202 | 0.4 | 0.084 | 0.097 | 0.185 | 0.127 | 0.142 | 0.136 | 0.109 |
| | Median, Weekly Average | 1.111 | 1.167 | 1.056 | 1.028 | 1.083 | 1.028 | 1.083 | 1.028 | 1.083 |
| | Minimum, Weekly Average | 1 | 1 | 1.028 | 1 | 1 | 1 | 1 | 1 | 1 |
| | Maximum, Weekly Average | 1.583 | 2.167 | 1.222 | 1.278 | 1.5 | 1.333 | 1.361 | 1.306 | 1.278 |
| | Maximum Daily Score | 2 | 4.167 | 1.5 | 1.667 | 1.833 | 1.333 | 2.333 | 1.833 | 1.333 |
| | #Subjects with score>4 | 0 | 1 | 0 | 0 | 0 | 0 | 0 | 0 | 0 |
| | Mean days/subject with score>4 | 0 | 0.143 | 0 | 0 | 0 | 0 | 0 | 0 | 0 |
| | Max days/subject with score>4 | 0 | 1 | 0 | 0 | 0 | 0 | 0 | 0 | 0 |

Fig. 6

|  |  | (Baseline) Week -1 | Week 1 | Week 2 | Week 3 | Week 4 | Week 5 | Week 6 | Week 7 | Week 8 |
|---|---|---|---|---|---|---|---|---|---|---|
| Cohort 1&2, Placebo (OC) | Number of Subjects | 7 | 7 | 7 | 7 | 6 | 6 | 6 | 5 | 5 |
|  | Mean, Weekly Average | 1.159 | 1.286 | 1.179 | 1.087 | 1.069 | 1.079 | 1.19 | 1.128 | 1.269 |
|  | Stdev, Weekly Average | 0.185 | 0.345 | 0.251 | 0.135 | 0.097 | 0.064 | 0.156 | 0.15 | 0.309 |
|  | Median, Weekly Average | 1.056 | 1.194 | 1.083 | 1 | 1.042 | 1.069 | 1.153 | 1.056 | 1.056 |
|  | Minimum, Weekly Average | 1 | 1.028 | 1 | 1 | 1 | 1 | 1 | 1 | 1.042 |
|  | Maximum, Weekly Average | 1.472 | 2 | 1.722 | 1.361 | 1.25 | 1.167 | 1.444 | 1.361 | 1.667 |
|  | Maximum Daily Score | 2.167 | 2.667 | 2.333 | 1.667 | 2 | 1.5 | 2.167 | 2.167 | 2 |
|  | #Subjects with score>4 | 0 | 0 | 0 | 0 | 0 | 0 | 0 | 0 | 0 |
|  | Mean days/subject with score>4 | 0 | 0 | 0 | 0 | 0 | 0 | 0 | 0 | 0 |
|  | Max days/subject with score>4 | 0 | 0 | 0 | 0 | 0 | 0 | 0 | 0 | 0 |
| Cohort 7, Placebo (Biopsy) | Number of Subjects | 7 | 7 | 7 | 7 | 7 | 7 | 7 | 7 | 7 |
|  | Mean, Weekly Average | 1.115 | 1.153 | 1.087 | 1.14 | 1.115 | 1.091 | 1.143 | 1.155 | 1.131 |
|  | Stdev, Weekly Average | 0.118 | 0.142 | 0.112 | 0.138 | 0.087 | 0.101 | 0.149 | 0.183 | 0.114 |
|  | Median, Weekly Average | 1.056 | 1.139 | 1.028 | 1.194 | 1.139 | 1.056 | 1.139 | 1.056 | 1.139 |
|  | Minimum, Weekly Average | 1 | 1 | 1 | 1 | 1 | 1 | 1 | 1 | 1 |
|  | Maximum, Weekly Average | 1.306 | 1.417 | 1.278 | 1.333 | 1.222 | 1.278 | 1.389 | 1.472 | 1.333 |
|  | Maximum Daily Score | 1.5 | 1.667 | 1.5 | 1.5 | 1.333 | 1.333 | 2.667 | 2.833 | 2.167 |
|  | #Subjects with score>4 | 0 | 0 | 0 | 0 | 0 | 0 | 0 | 0 | 0 |
|  | Mean days/subject with score>4 | 0 | 0 | 0 | 0 | 0 | 0 | 0 | 0 | 0 |
|  | Max days/subject with score>4 | 0 | 0 | 0 | 0 | 0 | 0 | 0 | 0 | 0 |

Fig. 6 (Continued)

| | | Average Weekly Change from Baseline | | | | | | | |
|---|---|---|---|---|---|---|---|---|---|
| | | Treatment Phase | | | | | | | |
| | | Week 1 | Week 2 | Week 3 | Week 4 | Week 5 | Week 6 | Week 7 | Week 8 |
| Cohort 1 150 mg (OC) | Number of Subjects | 8 | 8 | 8 | 8 | 8 | 8 | 8 | 8 |
| | Mean, Change from BL | 0.46 | 0.198 | 0.052 | 0.017 | 0 | 0.191 | 0.014 | 0.066 |
| | Stdev, Change from BL | 0.442 | 0.299 | 0.271 | 0.192 | 0.191 | 0.519 | 0.194 | 0.245 |
| | Median, Change from BL | 0.306 | 0.083 | 0.014 | 0.042 | 0 | 0.014 | -0.03 | -0.01 |
| | Minimum, Change from BL | 0 | -0.06 | -0.28 | -0.33 | -0.33 | -0.25 | -0.28 | -0.29 |
| | Maximum, Change from BL | 1.333 | 0.861 | 0.667 | 0.361 | 0.361 | 1.417 | 0.389 | 0.458 |
| Cohort 2 300 mg (OC) | Number of Subjects | 10 | 9 | 6 | 4 | 3 | 2 | 3 | 3 |
| | Mean, Change from BL | 0.497 | 0.246 | -0.18 | -0.06 | -0.17 | -0.32 | -0.31 | -0.33 |
| | Stdev, Change from BL | 0.672 | 0.532 | 0.198 | 0.138 | 0.247 | 0.098 | 0.039 | 0.056 |
| | Median, Change from BL | 0.431 | 0.083 | -0.25 | -0.03 | -0.25 | -0.32 | -0.31 | -0.33 |
| | Minimum, Change from BL | -0.33 | -0.33 | -0.39 | -0.22 | -0.36 | -0.39 | -0.33 | -0.39 |
| | Maximum, Change from BL | 1.806 | 1.306 | 0.083 | 0.056 | 0.111 | -0.25 | -0.28 | -0.28 |
| Cohort 7, 150 mg (Biopsy) | Number of Subjects | 7 | 7 | 7 | 7 | 7 | 7 | 7 | 7 |
| | Mean, Change from BL | 0.175 | -0.04 | -0.09 | 0.004 | -0.08 | -0.03 | -0.05 | -0.06 |
| | Stdev, Change from BL | 0.25 | 0.231 | 0.232 | 0.299 | 0.233 | 0.269 | 0.251 | 0.236 |
| | Median, Change from BL | 0.167 | 0.056 | -0.03 | 0 | 0 | 0 | 0.028 | 0 |
| | Minimum, Change from BL | -0.14 | -0.53 | -0.53 | -0.56 | -0.56 | -0.56 | -0.58 | -0.58 |
| | Maximum, Change from BL | 0.583 | 0.167 | 0.222 | 0.444 | 0.139 | 0.306 | 0.139 | 0.083 |

Fig. 7

| | | Average Weekly Change from Baseline |||||||| 
|---|---|---|---|---|---|---|---|---|---|
| | | Treatment Phase |||||||| 
| | | Week 1 | Week 2 | Week 3 | Week 4 | Week 5 | Week 6 | Week 7 | Week 8 |
| Cohorts 1&2, Placebo (OC) | Number of Subjects | 7 | 7 | 7 | 6 | 6 | 6 | 5 | 5 |
| | Mean, Change from BL | 0.127 | 0.02 | -0.07 | -0.12 | -0.11 | 0.005 | -0.08 | 0.058 |
| | Stdev, Change from BL | 0.227 | 0.142 | 0.068 | 0.151 | 0.18 | 0.12 | 0.17 | 0.188 |
| | Median, Change from BL | 0.028 | 0 | -0.06 | -0.04 | -0.08 | -0.01 | -0.03 | 0.042 |
| | Minimum, Change from BL | -0.08 | -0.19 | -0.17 | -0.39 | -0.39 | -0.17 | -0.28 | -0.22 |
| | Maximum, Change from BL | 0.528 | 0.25 | 0 | 0 | 0.111 | 0.167 | 0.083 | 0.264 |
| Cohort 7, Placebo (Biopsy) | Number of Subjects | 7 | 7 | 7 | 7 | 7 | 7 | 7 | 7 |
| | Mean, Change from BL | 0.038 | -0.03 | 0.025 | 5E-12 | -0.02 | 0.028 | 0.04 | 0.016 |
| | Stdev, Change from BL | 0.066 | 0.023 | 0.069 | 0.058 | 0.081 | 0.12 | 0.195 | 0.096 |
| | Median, Change from BL | 0.028 | -0.03 | 0 | 0 | -0.03 | -0.03 | -0 | 0 |
| | Minimum, Change from BL | -0.03 | -0.06 | -0.06 | -0.11 | -0.11 | -0.06 | -0.11 | -0.14 |
| | Maximum, Change from BL | 0.139 | 0 | 0.144 | 0.083 | 0.139 | 0.278 | 0.472 | 0.139 |

Fig. 7 (Continued)

|  | Pre-treatment Oral Challenge | | Post-treatment Oral Challenge | |
| --- | --- | --- | --- | --- |
|  | Gluten | Placebo | Gluten | Placebo |
| Cohort 1, Nex mg (OC) | | | | |
| Number of Subjects | 8 | 8 | 8 | 8 |
| Mean, Weekly Average | 1.412 | 1.146 | 1.586 | 1.184 |
| Stdev, Weekly Average | 0.369 | 0.174 | 0.716 | 0.294 |
| Median, Weekly Average | 1.246 | 1.069 | 1.359 | 1.083 |
| Minimum, Weekly Average | 1.056 | 1 | 1.028 | 1 |
| Maximum, Weekly Average | 1.972 | 1.417 | 3.222 | 1.861 |
| Maximum Daily Score | 2.5 | 2.833 | 4.667 | 2.167 |
| #Subjects with score>4 | 0 | 0 | 1 | 0 |
| Mean days/subject with score>4 | 0 | 0 | 0.375 | 0 |
| Max days/subject with score>4 | 0 | 0 | 1 | 0 |
| Cohort 1, Nex mg (OC) | | | | |
| Number of Subjects | 10 | 10 | 7 | 7 |
| Mean, Weekly Average | 1.452 | 1.272 | 1.579 | 1.179 |
| Stdev, Weekly Average | 0.423 | 0.215 | 0.759 | 0.313 |
| Median, Weekly Average | 1.292 | 1.292 | 1.194 | 1.028 |
| Minimum, Weekly Average | 1 | 1 | 1 | 1 |
| Maximum, Weekly Average | 2.222 | 1.583 | 3.111 | 1.861 |
| Maximum Daily Score | 3.5 | 3.333 | 5.167 | 2.5 |
| #Subjects with score>4 | 0 | 0 | 1 | 0 |
| Mean days/subject with score>4 | 0 | 0 | 0.286 | 0 |
| Max days/subject with score>4 | 0 | 0 | 1 | 0 |

Fig. 8

|  | Pre-treatment Oral Challenge | | Post-treatment Oral Challenge | |
| --- | --- | --- | --- | --- |
|  | Gluten | Placebo | Gluten | Placebo |
| Cohort 1&2, Placebo (OC) | | | | |
| Number of Subjects | 7 | 7 | 7 | 7 |
| Mean, Weekly Average | 1.444 | 1.397 | 1.575 | 1.143 |
| Stdev, Weekly Average | 0.439 | 0.243 | 0.42 | 0.192 |
| Median, Weekly Average | 1.278 | 1.389 | 1.417 | 1.056 |
| Minimum, Weekly Average | 1.056 | 1.083 | 1.139 | 1 |
| Maximum, Weekly Average | 2.306 | 1.75 | 2.389 | 1.528 |
| Maximum Daily Score | 2.667 | 2.5 | 3.333 | 1.667 |
| #Subjects with score>4 | 0 | 0 | 0 | 0 |
| Mean days/subject with score>4 | 0 | 0 | 0 | 0 |
| Max days/subject with score>4 | 0 | 0 | 0 | 0 |
| Screen Failures | | | | |
| Number of Subjects | 13 | 12 | | |
| Mean, Weekly Average | 1.728 | 1.391 | | |
| Stdev, Weekly Average | 0.73 | 0.419 | | |
| Median, Weekly Average | 1.639 | 1.208 | | |
| Minimum, Weekly Average | 1 | 1 | | |
| Maximum, Weekly Average | 3.433 | 2.306 | | |
| Maximum Daily Score | 6 | 3.333 | | |
| #Subjects with score>4 | 1 | 0 | | |
| Mean days/subject with score>4 | 0.154 | 0 | | |

Fig. 8 (Continued)

| Subject | Dose (mcg) | Doses | Visit | ELISA Reactivity | MAGPIX Reactivity | PC ELISA pg/mL | PC ELISA Stim. Index | CEF ELISA pg/ml | CEF SI ELISA Stim. Index | IFN-γ MAGPIX Fold/NIL | IL-2 MAGPIX Fold/NIL | IP-10 MAGPIX Fold/NIL |
|---|---|---|---|---|---|---|---|---|---|---|---|---|
| A | 150 | 16 | V4 | R | R | 76 | 40 | 2805 | 1437 | 3.15 | 7.66 | 12.00 |
|   |     |    | V23 | NR | NR | -5 | 0 | 2620 | 291 | 1.08 | 1.26 | 1.17 |
| B | 150 | 16 | V4 | R | R | 79 | 9 | 2482 | 264 | 2.73 | 3.14 | 10.90 |
|   |     |    | V23 | NR | NR | 6 | 3 | 2491 | 694 | 0.93 | 1.02 | 1.35 |
| C | 150 | 16 | V4 | R | R | 559 | 37 | 2099 | 137 | 14.94 | 43.95 | 16.35 |
|   |     |    | V23 | R | R | 1467 | 88 | 129 | 9 | 28.94 | 12.07 | 22.54 |
| D | 150 | 16 | V4 | R | R | 50 | 1 | 273 | 4 | 1.49 | 1.85 | 4.47 |
|   |     |    | V23 | NR | NR | 7 | 1 | 184 | 2 | 0.93 | 1.25 | 1.15 |
| E | 150 | 15 | V4 | R | R | 236 | 3 | 468 | 4 | 7.98 | 14.71 | 18.57 |
|   |     |    | V23 | R | R | 230 | 2 | 1484 | 6 | 4.39 | 3.39 | 13.67 |
| F | 150 | 16 | V4 | R | NR | 10 | 6 | 1230 | 623 | 1.00 | 0.90 | 0.93 |
|   |     |    | V23 | NR | ND | -6 | 0 | 946 | 81 | 0.95 | 1.45 | 1.08 |
| G | 150 | 16 | V4 | NR | ND | 0 | 1 | 388 | 200 | ND | ND | ND |
|   |     |    | V23 | NR | ND | 0 | 1 | 582 | 299 | 0.22 | 0.66 | 0.01 |
| H | 150 | 16 | V2 | R | ND | 55 | 1 | 443 | 4 | ND | ND | ND |
|   |     |    | V23 | NR | ND | 6 | 1 | 539 | 3 | ND | ND | ND |

PC= peptide composition

Fig. 13

| Subject | Dose (mcg) | Doses | Visit | ELISA Reactivity | MAGPIX Reactivity | PC ELISA pg/mL | PC ELISA Stim. Index | CEF ELISA pg/ml | CEF SI ELISA Stim. Index | IFN-γ MAGPIX Fold/NIL | IL-2 MAGPIX Fold/NIL | IP-10 MAGPIX Fold/NIL |
|---|---|---|---|---|---|---|---|---|---|---|---|---|
| I | 300 | 16 | V4 | NR | NR | 0 | 1 | 200 | 103 | 1.49 | 1.85 | 1.23 |
|  |  |  | V23 | NR | NR | 0 | 1 | 203 | 105 | 1.08 | 1.11 | 0.93 |
| J | 300 | 16 | V4 | R | NR | 8 | 5 | 1253 | 643 | 1.18 | 1.46 | 1.32 |
|  |  |  | V23 | NR | NR | -4 | 0 | 763 | 135 | 1.23 | 1.08 | 0.56 |
| K | 300 | 5 | V4 | R | ND | 149 | 77 | 339 | 175 | ND | ND | ND |
|  |  |  | V23 | NR | NR | 0 | 1 | 250 | 129 | 1.02 | 1.06 | 1.99 |
| L | 300 | 4 | V4 | R | ND | 127 | 4 | 570 | 16 | ND | ND | ND |
|  |  |  | V23 | NR | NR | -7 | 0 | 537 | 58 | 0.80 | 0.60 | 1.00 |

PC= peptide composition

Fig. 14

| Subject | Dose (mcg) | Doses | Visit | ELISA Reactivity | MAGPIX Reactivity | PC ELISA pg/mL | PC ELISA Stim. Index | CEF ELISA pg/ml | CEF SI ELISA Stim. Index | IFN-γ MAGPIX Fold/NiL | IL-2 MAGPIX Fold/NiL | IP-10 MAGPIX Fold/NiL |
|---|---|---|---|---|---|---|---|---|---|---|---|---|
| M | 0 | 16 | V2 | R | R | 186.73 | 5.57 | 1602.95 | 40.23 | 3.54 | 5.72 | 6.02 |
|   |   |   | V23 | R | R | 51.11 | 5.84 | 408.79 | 39.73 | 2.53 | 4.68 | 6.33 |
| N | 0 | 16 | V2 | R | R | 25.33 | 7.48 | 753.07 | 193.64 | 1.90 | 4.07 | 7.38 |
|   |   |   | V23 | NR | R | 6.58 | 1.52 | 1601.98 | 128.09 | 2.33 | 6.11 | 3.18 |
| O | 0 | 16 | V2 | R | ND | 183.59 | 26.88 | 475.56 | 68.03 | ND | ND | ND |
|   |   |   | V23 | R | R | 272.61 | 128.53 | 700.20 | 328.56 | 5.99 | 8.44 | 6.60 |
| P | 0 | 15 | V4 | R | NR | 27.95 | 2.86 | 1001.75 | 67.69 | 0.72 | 0.94 | 0.91 |
|   |   |   | V23 | NR | R | 7.79 | 1.06 | 192.55 | 2.49 | 2.39 | 1.38 | 1.76 |
| Q | 0 | 10 | V4 | R | R | 17.76 | 2.10 | 536.69 | 34.35 | 0.99 | 1.06 | 3.66 |
|   |   |   | V23 | NR | NR | -3.27 | 0.82 | 151.79 | 9.31 | 0.80 | 1.00 | 0.97 |
| R | 0 | 16 | V4 | R | R | 637.07 | 327.20 | 1959.30 | 1004.22 | 8.15 | 27.25 | 16.89 |
|   |   |   | V23 | R | R | 39.79 | 21.38 | 442.77 | 227.71 | 2.43 | 5.86 | 13.65 |
| S | 0 | 5 | V2 | R | R | 56.41 | 1.43 | -17.32 | 0.87 | 2.80 | 12.98 | 11.36 |
|   |   |   | V23 | R | R | 30.31 | 1.39 | -7.23 | 0.91 | 1.75 | 4.87 | 7.76 |

PC= peptide composition

Fig. 15

SEQUENCE LISTING

```
<160> NUMBER OF SEQ ID NOS: 9

<210> SEQ ID NO 1
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 1

Glu Leu Gln Pro Phe Pro Gln Pro Glu Leu Pro Tyr Pro Gln Pro Gln
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 2

Glu Gln Pro Phe Pro Gln Pro Glu Gln Pro Phe Pro Trp Gln Pro
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 3

Glu Pro Glu Gln Pro Ile Pro Glu Gln Pro Gln Pro Tyr Pro Gln Gln
1               5                   10                  15

<210> SEQ ID NO 4
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 4

Pro Phe Pro Gln Pro Glu Leu Pro Tyr
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 5

Pro Gln Pro Glu Leu Pro Tyr Pro Gln
1               5
```

```
<210> SEQ ID NO 6
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 6

Pro Phe Pro Gln Pro Glu Gln Pro Phe
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 7

Pro Gln Pro Glu Gln Pro Phe Pro Trp
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 8

Glu Gln Pro Ile Pro Glu Gln Pro Gln
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 9

Pro Ile Pro Glu Gln Pro Gln Pro Tyr
1               5
```

DOSAGE OF A GLUTEN PEPTIDE COMPOSITION

RELATED APPLICATIONS

This application is a national stage filing under 35 U.S.C. § 371 of International Application No. PCT/US2014/054959, filed Sep. 10, 2014, and entitled "DOSAGE OF A GLUTEN PEPTIDE COMPOSITION," which claims the benefit under 35 U.S.C. § 119(e) of U.S. provisional application Ser. No. 61/876,172, filed Sep. 10, 2013, U.S. provisional application Ser. No. 61/983,989, filed Apr. 24, 2014, and U.S. provisional application Ser. No. 62/014,666, filed Jun. 19, 2014, the contents of each of which are hereby incorporated by reference in their entireties.

BACKGROUND

Celiac disease, also known as coeliac disease or Celiac sprue (Coeliac sprue), affects approximately 1% of people in Europe and North America. In many of those affected, Celiac disease is unrecognised, but this clinical oversight is now being rectified with greater clinical awareness. A gluten free diet is the only currently approved treatment for Celiac disease, and because regular ingestion of as little as 50 mg of gluten (equivalent to $\frac{1}{100}^{th}$ of a standard slice of bread) can damage the small intestine; chronic inflammation of the small bowel is commonplace in subjects on a gluten free diet. Persistent inflammation of the small intestine has been shown to increase the risk of cancer, osteoporosis and death. As gluten is so widely used, for example, in commercial soups, sauces, ice-creams, etc., maintaining a gluten-free diet is difficult.

Celiac disease occurs in genetically susceptible individuals who possess either HLA-DQ2.5 (encoded by the genes HLA-DQA1*05 and HLA-DQB1*02) accounting for about 90% of individuals, HLA-DQ2.2 (encoded by the genes HLA-DQA1*02 and HLA-DQB1*02), or HLA-DQ8 (encoded by the genes HLA-DQA1*03 and HLA-DQB1*0302). Without wishing to be bound by theory, it is believed that such individuals mount an inappropriate HLA-DQ2- and/or DQ8-restricted CD4$^+$ T cell-mediated immune response to peptides derived from the aqueous-insoluble proteins of wheat flour, gluten, and related proteins in rye and barley.

SUMMARY

Described herein are specific dosages and dosage schedules of a composition for use in treating subjects with Celiac disease. In some aspects, any one of the compositions provided can include a first peptide comprising the amino acid sequence PFPQPELPY (SEQ ID NO: 4) and the amino acid sequence PQPELPYPQ (SEQ ID NO: 5), a second peptide comprising the amino acid sequence PFPQPEQPF (SEQ ID NO: 6) and the amino acid sequence PQPEQPFPW (SEQ ID NO: 7), and a third peptide comprising the amino acid sequence EQPIPEQPQ (SEQ ID NO: 8) and the amino acid sequence PIPEQPQPY (SEQ ID NO: 9), optionally wherein the N-terminus of one or more of the peptides (e.g., the N-terminus of each of the peptides) comprises a pyroglutamate and the C-terminus of one or more of the peptides (e.g., the C-terminus of each of the peptides) comprises an amino acid having an amidated carboxyl group. Without wishing to be bound by theory as above-mentioned SEQ ID NOs: 4-9 are thought to be T-cell epitopes. In some embodiments, the composition includes a first peptide comprising the amino acid sequence ELQPFPQPELPYPQPQ (SEQ ID NO: 1), wherein the N-terminal glutamate is a pyroglutamate and the carboxyl group of the C-terminal glutamine is amidated; a second peptide comprising the amino acid sequence EQPFPQPEQPFPWQP (SEQ ID NO: 2), wherein the N-terminal glutamate is a pyroglutamate and the carboxyl group of the C-terminal proline is amidated; and a third peptide comprising the amino acid sequence EPEQPIPEQPQPYPQQ (SEQ ID NO: 3), wherein the N-terminal glutamate is a pyroglutamate and the carboxyl group of the C-terminal glutamine is amidated. It is believed that administration of the compositions provided herein in the dosages and dosage schedules described herein to a subject with Celiac disease will induce immune tolerance in the subject such that the subject may consume or come into contact with at least wheat, rye, barley and optionally oats without a significant T cell response which would normally lead to symptoms of Celiac disease.

Accordingly, aspects of the disclosure relate to compositions and methods for treating a subject with Celiac disease.

In some aspects, the disclosure relates to a method for treating Celiac disease in a subject, the method comprising administering any one of the compositions provided herein to the subject. In some embodiments, the (a) first peptide comprising the amino acid sequence PFPQPELPY (SEQ ID NO: 4) and the amino acid sequence PQPELPYPQ (SEQ ID NO: 5), optionally wherein the N-terminus comprises a pyroglutamate (e.g., any N-terminal glutamate is a pyroglutamate) and the C-terminus is amidated (e.g., any C-terminal glutamine is amidated); (b) a second peptide comprising the amino acid sequence PFPQPEQPF (SEQ ID NO: 6) and the amino acid sequence PQPEQPFPW (SEQ ID NO: 7), optionally wherein the N-terminus comprises a pyroglutamate (e.g., any N-terminal glutamate is a pyroglutamate) and the C-terminus is amidated (e.g., any C-terminal proline is amidated); and (c) a third peptide comprising the amino acid sequence EQPIPEQPQ (SEQ ID NO: 8) and the amino acid sequence PIPEQPQPY (SEQ ID NO: 9), optionally wherein the N-terminus comprises a pyroglutamate (e.g., any N-terminal glutamate is a pyroglutamate) and the C-terminus is amidated (e.g., any C-terminal glutamine is amidated); and wherein 50 micrograms of the first peptide and an equimolar amount of each of the second and third peptides are administered once or twice per week to the subject. In some aspects, the disclosure relates to a method for treating Celiac disease in a subject, the method comprising administering to the subject: (a) first peptide comprising the amino acid sequence ELQPFPQPELPYPQPQ (SEQ ID NO: 1), wherein the N-terminal glutamate is a pyroglutamate and the C-terminal glutamine is amidated; (b) a second peptide comprising the amino acid sequence EQPFPQPEQPFPWQP (SEQ ID NO: 2), wherein the N-terminal glutamate is a pyroglutamate and the C-terminal proline is amidated; and (c) a third peptide comprising the amino acid sequence EPEQPIPEQPQPYPQQ (SEQ ID NO: 3), wherein the N-terminal glutamate is a pyroglutamate and the C-terminal glutamine is amidated; wherein 50 micrograms of the first peptide and an equimolar amount of each of the second and third peptides are administered once or twice per week to the subject. In some embodiments, the 50 micrograms of the first peptide and the equimolar amount of each of the second and third peptides are administered twice per week to the subject. In some embodiments, the 50 micrograms of the first peptide and the equimolar amount of each of the second and third peptides are administered once per week to the subject.

In some embodiments of any one of the methods provided, the first, second and third peptides are in equimolar amounts in a composition, and the composition is administered to the subject. In some embodiments of any one of the methods provided, the first, second and third peptides are each in an amount of 50 micrograms in the composition. In some embodiments of any one of the methods provided, the first, second and third peptides or the composition are/is administered intradermally. In some embodiments of any one of the methods provided, the first, second and third peptides or the composition are/is administered as a bolus by intradermal injection. In some embodiments of any one of the methods provided, the first, second and third peptides or the composition are/is formulated as a sterile, injectable solution. In some embodiments of any one of the methods provided, the sterile, injectable solution is sodium chloride. In some embodiments of any one of the methods provided, the sodium chloride is sterile sodium chloride 0.9% USP. In some embodiments of any one of the methods provided, the first, second and third peptides or the composition are/is administered for eight weeks. In some embodiments of any one of the methods provided, the first, second and third peptides or the composition are/is administered for four weeks. In some of these embodiments of any one of the methods provided, when administration is for four weeks, the first, second and third peptides are administered biweekly for the four weeks. In some embodiments of any one of the methods provided, the first, second and third peptides or the composition are/is administered for three weeks. In some of these embodiments of any one of the methods provided, when administration is for three weeks, the first, second and third peptides are administered weekly for the three weeks. In some embodiments of any one of the methods provided, the subject is HLA-DQ2.5 positive. In some embodiments of any one of the methods provided, the subject is on a gluten-free diet.

In some aspects, the disclosure relates to a method for treating Celiac disease in a subject, the method comprising administering to the subject: (a) first peptide comprising the amino acid sequence PFPQPELPY (SEQ ID NO: 4) and the amino acid sequence PQPELPYPQ (SEQ ID NO: 5), optionally wherein the N-terminus comprises a pyroglutamate (e.g., any N-terminal glutamate is a pyroglutamate) and the C-terminus is amidated (e.g., any C-terminal glutamine is amidated); (b) a second peptide comprising the amino acid sequence PFPQPEQPF (SEQ ID NO: 6) and the amino acid sequence PQPEQPFPW (SEQ ID NO: 7), optionally wherein the N-terminus comprises a pyroglutamate (e.g., any N-terminal glutamate is a pyroglutamate) and the C-terminus is amidated (e.g., any C-terminal proline is amidated); and (c) a third peptide comprising the amino acid sequence EQPIPEQPQ (SEQ ID NO: 8) and the amino acid sequence PIPEQPQPY (SEQ ID NO: 9), optionally wherein the N-terminus comprises a pyroglutamate (e.g., any N-terminal glutamate is a pyroglutamate) and the C-terminus is amidated (e.g., any C-terminal glutamine is amidated); and wherein 100 micrograms of the first peptide and an equimolar amount of each of the second and third peptides are administered once or twice per week to the subject. In some aspects, the disclosure relates to a method for treating Celiac disease in a subject, the method comprising administering to the subject: (a) first peptide comprising the amino acid sequence ELQPFPQPELPYPQPQ (SEQ ID NO: 1), wherein the N-terminal glutamate is a pyroglutamate and the C-terminal glutamine is amidated; (b) a second peptide comprising the amino acid sequence EQPFPQPEQPFPWQP (SEQ ID NO: 2), wherein the N-terminal glutamate is a pyroglutamate and the C-terminal proline is amidated; and (c) a third peptide comprising the amino acid sequence EPEQPIPEQPQPYPQQ (SEQ ID NO: 3), wherein the N-terminal glutamate is a pyroglutamate and the C-terminal glutamine is amidated; wherein 100 micrograms of the first peptide and an equimolar amount of each of the second and third peptides are administered once or twice per week to the subject. In some embodiments, the 100 micrograms of the first peptide and the equimolar amount of each of the second and third peptides are administered twice per week to the subject. In some embodiments, the 100 micrograms of the first peptide and the equimolar amount of each of the second and third peptides are administered once per week to the subject.

In some embodiments of any one of the methods provided, the first, second and third peptides are in equimolar amounts in a composition, and the composition is administered to the subject. In some embodiments of any one of the methods provided, the first, second and third peptides are each in an amount of 100 micrograms in the composition. In some embodiments of any one of the methods provided, the first, second and third peptides or the composition are/is administered intradermally. In some embodiments of any one of the methods provided, the first, second and third peptides or the composition are/is administered as a bolus by intradermal injection. In some embodiments of any one of the methods provided, the first, second and third peptides or the composition are/is formulated as a sterile, injectable solution. In some embodiments of any one of the methods provided, the sterile, injectable solution is sodium chloride. In some embodiments, the sodium chloride is sterile sodium chloride 0.9% USP. In some embodiments of any one of the methods provided, the first, second and third peptides or the composition are/is administered for eight weeks. In some embodiments of any one of the methods provided, the first, second and third peptides or the composition are/is administered for four weeks. In some of these embodiments of any one of the methods provided, when administration is for four weeks, the first, second and third peptides are administered biweekly for the four weeks. In some embodiments of any one of the methods provided, the subject is HLA-DQ2.5 positive. In some embodiments of any one of the methods provided, the subject is on a gluten-free diet.

In some embodiments of any one of the methods above, the method further comprises assessing immune tolerance after administration of the first, second and third peptides. In some embodiments of any one of the methods provided, assessing immune tolerance comprises measuring a T cell response to gluten and/or to any one of the compositions provided herein, such as one that comprises the first, second and third peptides provided herein, in a sample comprising T cells from the subject. In some embodiments of any one of the methods provided, measuring the T cell response comprises contacting the sample with gluten and/or any one of the compositions provided, such as one that comprises the first, second and third peptides provided herein, and measuring the T cell response in the sample after the contacting. In some embodiments of any one of the methods provided, the T cell response is measured by measuring a level of IFN-γ. In some embodiments of any one of the methods provided, a subject is identified as tolerized if IFN-γ levels <7.2 pg/mL or as otherwise provided in the Examples. In some embodiments, measuring the level of IFN-γ comprises an immuno-based assay. In some embodiments, the immuno-based assay comprises an ELISA.

In other aspects, the disclosure relates to a composition, comprising: (a) first peptide comprising the amino acid sequence PFPQPELPY (SEQ ID NO: 4) and the amino acid sequence PQPELPYPQ (SEQ ID NO: 5), optionally wherein the N-terminus comprises a pyroglutamate (e.g., any N-terminal glutamate is a pyroglutamate) and the C-terminus is amidated (e.g., any C-terminal glutamine is amidated); (b) a second peptide comprising the amino acid sequence PFPQPEQPF (SEQ ID NO: 6) and the amino acid sequence PQPEQPFPW (SEQ ID NO: 7), optionally wherein the N-terminus comprises a pyroglutamate (e.g., any N-terminal glutamate is a pyroglutamate) and the C-terminus is amidated (e.g., any C-terminal proline is amidated); and (c) a third peptide comprising the amino acid sequence EQPIPEQPQ (SEQ ID NO: 8) and the amino acid sequence PIPEQPQPY (SEQ ID NO: 9), optionally wherein the N-terminus comprises a pyroglutamate (e.g., any N-terminal glutamate is a pyroglutamate) and the C-terminus is amidated (e.g., any C-terminal glutamine is amidated); wherein 50 micrograms of the first peptide and an equimolar amount of each of the second and third peptides are present in the composition. In other aspects, the disclosure relates to a composition, comprising: (a) a first peptide comprising the amino acid sequence ELQPFPQPELPYPQPQ (SEQ ID NO: 1), wherein the N-terminal glutamate is a pyroglutamate and the C-terminal glutamine is amidated; (b) a second peptide comprising the amino acid sequence EQPFPQPEQPFP-WQP (SEQ ID NO: 2), wherein the N-terminal glutamate is a pyroglutamate and the C-terminal proline is amidated; and (c) a third peptide comprising the amino acid sequence EPEQPIPEQPQPYPQQ (SEQ ID NO: 3), wherein the N-terminal glutamate is a pyroglutamate and the C-terminal glutamine is amidated; wherein 50 micrograms of the first peptide and an equimolar amount of each of the second and third peptides are present in the composition. In yet other aspects, the disclosure relates to a composition, comprising: (a) first peptide comprising the amino acid sequence PFPQPELPY (SEQ ID NO: 4) and the amino acid sequence PQPELPYPQ (SEQ ID NO: 5), optionally wherein the N-terminus comprises a pyroglutamate (e.g., any N-terminal glutamate is a pyroglutamate) and the C-terminus is amidated (e.g., any C-terminal glutamine is amidated); (b) a second peptide comprising the amino acid sequence PFPQPEQPF (SEQ ID NO: 6) and the amino acid sequence PQPEQPFPW (SEQ ID NO: 7), optionally wherein the N-terminus comprises a pyroglutamate (e.g., any N-terminal glutamate is a pyroglutamate) and the C-terminus is amidated (e.g., any C-terminal proline is amidated); and (c) a third peptide comprising the amino acid sequence EQPIPEQPQ (SEQ ID NO: 8) and the amino acid sequence PIPEQPQPY (SEQ ID NO: 9), optionally wherein the N-terminus comprises a pyroglutamate (e.g., any N-terminal glutamate is a pyroglutamate) and the C-terminus is amidated (e.g., any C-terminal glutamine is amidated); wherein 100 micrograms of the first peptide and an equimolar amount of each of the second and third peptides are present in the composition. In other aspects of the disclosure, the composition, comprises: (a) a first peptide comprising the amino acid sequence ELQPFPQPELPYPQPQ (SEQ ID NO: 1), wherein the N-terminal glutamate is a pyroglutamate and the C-terminal glutamine is amidated; (b) a second peptide comprising the amino acid sequence EQPFPQPEQPFP-WQP (SEQ ID NO: 2), wherein the N-terminal glutamate is a pyroglutamate and the C-terminal proline is amidated; and (c) a third peptide comprising the amino acid sequence EPEQPIPEQPQPYPQQ (SEQ ID NO: 3), wherein the N-terminal glutamate is a pyroglutamate and the C-terminal glutamine is amidated; wherein 100 micrograms of the first peptide and an equimolar amount of each of the second and third peptides are present in the composition.

In some embodiments of any one of the compositions provided, the first, second and third peptides are in equimolar amounts in the composition. In some embodiments of any one of the compositions provided, the first, second and third peptides are each in an amount of 50 micrograms in the composition. In some embodiments of any one of the compositions provided, the first, second and third peptides are each in an amount of 100 micrograms in the composition. In some embodiments of any one of the compositions provided, the composition is formulated for intradermal administration to a subject. In some embodiments of any one of the compositions provided, the composition is formulated as a bolus for intradermal injection to a subject. In some embodiments of any one of the compositions provided, the composition is formulated as a sterile, injectable solution. In some embodiments of any one of the compositions provided, the sterile, injectable solution is sodium chloride. In some embodiments of any one of the compositions provided, the sodium chloride is sterile sodium chloride 0.9% USP. In some embodiments of any one of the compositions provided, the composition is comprised in a kit. In some embodiments, the first, second and third peptides are contained in the same container in the kit. In some embodiments, the first, second and third peptides are contained in separate containers in the kit.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 5 is a table showing responsiveness and tolerance by ex vivo whole blood cytokine release stimulated by immuno-dominant gluten-derived T cell epitopes before and after celiac disease patients are treated with the peptide composition.

FIG. 6 is a table showing the symptom scores during dosing.

FIG. 7 is a table showing the symptom scores during dosing as changed from baseline.

FIG. 8 is a table showing the symptom scores during gluten challenge.

FIG. 13 is a table showing ELISA and MAGPIX data from whole blood contacted with peptide composition or controls in samples collected from cohort 1 (150 micrograms peptide composition) after gluten oral challenge.

FIG. 14 is a table showing ELISA and MAGPIX data from whole blood contacted with peptide composition or controls in samples collected from cohort 2 (300 micrograms peptide composition) after gluten oral challenge.

FIG. 15 is a table showing ELISA and MAGPIX data from whole blood contacted with peptide composition or controls in samples collected from placebo cohort (cohorts 1 and 2 placebo) after gluten oral challenge.

DETAILED DESCRIPTION

General Techniques and Definitions

Figure 1:
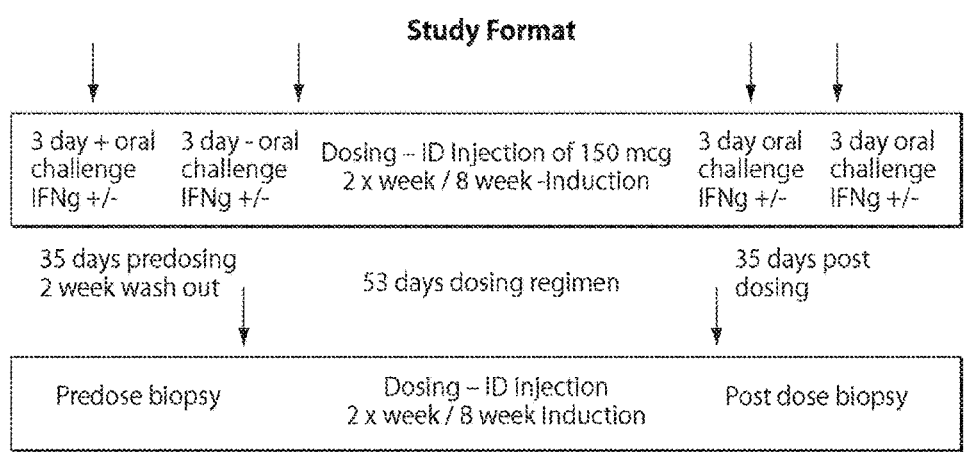
FIG. 1 is a diagram of the study format in Example 3.

Unless specifically defined otherwise, all technical and scientific terms used herein shall be taken to have the same meaning as commonly understood by one of ordinary skill in the art (e.g., in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984); J. Sambrook et al., Molecular Cloning: A Laboratory Manual, Cold Spring Harbour Laboratory Press (1989); T. A. Brown (editor), Essential Molecular Biology: A Practical Approach, Volumes 1 and 2, IRL Press (1991); D. M. Glover and B. D. Hames (editors), DNA Cloning: A Practical Approach, Volumes 1-4, IRL Press (1995 and 1996); F. M. Ausubel et al. (editors), Current Protocols in Molecular Biology, Greene Pub. Associates and Wiley-Interscience (1988, including all updates until present); Ed Harlow and David Lane (editors) Antibodies: A Laboratory Manual, Cold Spring Harbour Laboratory, (1988); and J. E. Coligan et al. (editors), Current Protocols in Immunology, John Wiley & Sons (including all updates until present).

The term "Celiac disease" refers to an immune-mediated systemic disorder elicited by gluten and related prolamines in genetically susceptible individuals, characterized by the presence of a variable combination of gluten-dependent clinical manifestations, celiac disease-specific antibodies, human leukocyte antigen (HLA)-DQ2 and HLA-DQ8 haplotypes, and enteropathy. The disease encompasses a spectrum of conditions characterised by an inappropriate CD4$^+$ T cell response to gluten, or a peptide thereof. The severe form of celiac disease is characterised by a flat small intestinal mucosa (hyperplastic villous atrophy) and other forms are characterised by milder histological abnormalities in the small intestine, such as intra-epithelial lymphocytosis without villous atrophy. Serological abnormalities associated with celiac disease include the presence of autoantibodies specific for tissue transglutaminase-2, and antibodies specific for deamidated gluten-derived peptides. The clinical manifestations associated with celiac disease can include fatigue, chronic diarrhea, malabsorption of nutrients, weight loss, abdominal distension, anaemia as well as a substantially enhanced risk for the development of osteoporosis and intestinal malignancies (lymphoma and carcinoma). A central feature in the current definitive diagnosis of celiac disease is that intestinal histology, celiac disease-specific serology and clinical abnormalities resolve or improve with exclusion of dietary gluten.

The terms "human leukocyte antigen" and "HLA" are here defined as a genetic fingerprint expressed on human white blood cells, composed of proteins that play a critical role in activating the body's immune system to respond to foreign organisms. In humans and other animals, the HLA is also collectively referred to as the "major histocompatibility complex" (MHC).

The term "subject" includes inter alia an individual, patient, target, host or recipient regardless of whether the subject is a human or non-human animal including mammalian species and also avian species. The term "subject", therefore, includes a human, non-human primate (for example, gorilla, marmoset, African Green Monkey), livestock animal (for example, sheep, cow, pig, horse, donkey, goat), laboratory test animal (for example, rat, mouse, rabbit, guinea pig, hamster), companion animal (for example, dog, cat), captive wild animal (for example, fox, deer, game animals) and avian species including poultry birds (for example, chickens, ducks, geese, turkeys). The preferred subject, however, is a human. In some embodiments, the subject is a human on a gluten-free diet. In some embodiments, the subject is a human who is HLA-DQ2.5 positive. In some embodiments, the subject is a human who is HLA-DQ2.5 positive and HLA-DQ8 negative. In some embodiments, the subject is human who is HLA-DQ2.5 positive and HLA-DQ8 positive.

Peptides

The terms "peptide", "polypeptide", and "protein" can generally be used interchangeably and also encompass pharmaceutical salts thereof. However, the term "peptide" is typically used to refer to relatively short molecules comprising less than 50, more preferably less than 25, amino acids.

The overall length of each peptide defined herein may be, for example, 7 to 50 amino acids, such as 7, 8, 9 10, 11, 12, 13, 14, 15, 16, 17, 18, 19, 20, 21, 22, 23, 24, 25, 30, 35, 40, 45, or 50 amino acids, or any integer in between. It is contemplated that shorter peptides may prove useful, particularly those that are 20 or fewer amino acids in length, in therapeutics to reduce the likelihood of anaphylaxis but longer peptides with multiple epitopes are likely to be as effective as multiple short peptides, for example, in functional T cell-based diagnostics in vitro.

It is believed that the peptides of the disclosure, such as those that comprise SEQ ID NOs: 1, 2, and 3, are capable of generating a T cell response in a subject having Celiac disease. Without wishing to be bound by theory, T cell responses in a subject with Celiac disease are thought to be caused by T-cell receptor ligation of the minimal T cell epitopes present in SEQ ID NOs: 1, 2, and 3 that are presented by HLA-DQ2.5 on the surface of antigen presenting cells.

In some embodiments, a peptide is modified during or after translation or synthesis (for example, by farnesylation, prenylation, myristoylation, glycosylation, palmitoylation, acetylation, phosphorylation [such as phosphotyrosine, phosphoserine or phosphothreonine], amidation, derivatisation by known protecting/blocking groups, proteolytic cleavage, linkage to an antibody molecule or other cellular ligand, and the like). Any of the numerous chemical modification methods known within the art may be utilised including, but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

The phrases "protecting group" and "blocking group" as used herein, refers to modifications to the peptide, which protect it from undesirable chemical reactions, particularly in vivo. Examples of such protecting groups include esters of carboxylic acids and boronic acids, ethers of alcohols and acetals, and ketals of aldehydes and ketones. Examples of suitable groups include acyl protecting groups such as, for example, furoyl, formyl, adipyl, azelayl, suberyl, dansyl, acetyl, theyl, benzoyl, trifluoroacetyl, succinyl and methoxysuccinyl; aromatic urethane protecting groups such as, for example, benzyloxycarbonyl (Cbz); aliphatic urethane protecting groups such as, for example, t-butoxycarbonyl (Boc) or 9-fluorenylmethoxy-carbonyl (FMOC); pyroglutamate and amidation. Many other modifications providing increased potency, prolonged activity, ease of purification, and/or increased half-life will be known to the person skilled in the art.

The peptides may comprise one or more modifications, which may be natural post-translation modifications or artificial modifications. The modification may provide a chemical moiety (typically by substitution of a hydrogen, for example, of a C—H bond), such as an amino, acetyl, acyl, amide, carboxy, hydroxy or halogen (for example, fluorine) group, or a carbohydrate group. Typically, the modification may be present on the N- and/or C-terminus. Furthermore, one or more of the peptides may be PEGylated, where the PEG (polyethyleneoxy group) provides for enhanced lifetime in the blood stream. One or more of the peptides may also be combined as a fusion or chimeric protein with other proteins, or with specific binding agents that allow targeting to specific moieties on a target cell. The peptide may also be chemically modified at the level of amino acid side chains, of amino acid chirality, and/or of the peptide backbone.

Particular changes may be made to the peptides to improve resistance to degradation or optimise solubility properties or otherwise improve bioavailability compared to the parent peptide, thereby providing peptides having similar or improved therapeutic, diagnostic and/or pharmacokinetic properties. A preferred such modification includes the use of an N-terminal pyroglutamate and/or a C-terminal amide (such as the respective N-terminal pyroglutamate and C-terminal glutamine of SEQ ID NOs: 1, 2, and 3). Such modifications significantly increase the half-life and bioavailability of the peptides compared to the parent peptides having a free N- and C-terminus.

In a particular embodiment, a composition comprising a first peptide comprising the amino acid sequence ELQP-FPQPELPYPQPQ (SEQ ID NO: 1), wherein the N-terminal glutamate is a pyroglutamate and the C-terminal glutamine is amidated (i.e., the free C-terminal COO is amidated); a second peptide comprising the amino acid sequence EQP-FPQPEQPFPWQP (SEQ ID NO: 2), wherein the N-terminal glutamate is a pyroglutamate and the C-terminal proline is amidated (i.e., the free C-terminal COO is amidated); and a third peptide comprising the amino acid sequence EPEQPIPEQPQPYPQQ (SEQ ID NO: 3), wherein the N-terminal glutamate is a pyroglutamate and the C-terminal glutamine is amidated (i.e., the free C-terminal COO is amidated) is contemplated. In some embodiments, the first, second and/or third peptides consist essentially of or consist of the amino acid sequence of SEQ ID NO: 1, 2, or 3, respectively. Compositions are further described herein.

In another embodiment, a composition comprising first peptide comprising the amino acid sequence PFPQPELPY (SEQ ID NO: 4) and the amino acid sequence PQPELPYPQ (SEQ ID NO: 5), optionally wherein the N-terminus comprises a pyroglutamate (e.g., any N-terminal glutamate is a pyroglutamate) and the C-terminus is amidated (e.g., any C-terminal glutamine is amidated); a second peptide comprising the amino acid sequence PFPQPEQPF (SEQ ID NO: 6) and the amino acid sequence PQPEQPFPW (SEQ ID NO: 7), optionally wherein the N-terminus comprises a pyroglutamate (e.g., any N-terminal glutamate is a pyroglutamate) and the C-terminus is amidated (e.g., any C-terminal proline is amidated); and a third peptide comprising the amino acid sequence EQPIPEQPQ (SEQ ID NO: 8) and the amino acid sequence PIPEQPQPY (SEQ ID NO: 9), optionally wherein the N-terminus comprises a pyroglutamate (e.g., any N-terminal glutamate is a pyroglutamate) and the C-terminus is amidated (e.g., any C-terminal proline is amidated) is contemplated.

Certain peptides described herein may exist in particular geometric or stereoisomeric forms. The present disclosure contemplates all such forms, including cis-(Z) and trans-(E) isomers, R- and S-enantiomers, diastereomers, (D)-isomers, (L)-isomers, the racemic mixtures thereof, and other mixtures thereof, as, falling within the scope of the disclosure. Additional asymmetric carbon atoms may be present in a substituent, such as an alkyl group. All such isomers, as well as mixtures thereof, are intended to be included in this disclosure. In another example, to prevent cleavage by peptidases, any one or more of the peptides may include a non-cleavable peptide bond in place of a particularly sensitive peptide bond to provide a more stable peptide. Such non-cleavable peptide bonds may include beta amino acids.

In certain embodiments, any one or more of the peptides may include a functional group, for example, in place of the scissile peptide bond, which facilitates inhibition of a serine-, cysteine- or aspartate-type protease, as appropriate. For example, the disclosure includes a peptidyl diketone or a peptidyl keto ester, a peptide haloalkylketone, a peptide sulfonyl fluoride, a peptidyl boronate, a peptide epoxide, a peptidyl diazomethane, a peptidyl phosphonate, isocoumarins, benzoxazin-4-ones, carbamates, isocyantes, isatoic anhydrides or the like. Such functional groups have been provided in other peptide molecules, and general routes for their synthesis are known.

The peptides may be in a salt form, preferably, a pharmaceutically acceptable salt form. "A pharmaceutically acceptable salt form" includes the conventional non-toxic salts or quaternary ammonium salts of a peptide, for example, from non-toxic organic or inorganic acids. Conventional non-toxic salts include, for example, those derived from inorganic acids such as hydrochloride, hydrobromic, sulphuric, sulfonic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

Peptide Production

The peptides can be prepared in any suitable manner. For example, the peptides can be recombinantly and/or synthetically produced.

The peptides may be synthesised by standard chemistry techniques, including synthesis by an automated procedure using a commercially available peptide synthesiser. In general, peptides may be prepared by solid-phase peptide synthesis methodologies which may involve coupling each protected amino acid residue to a resin support, preferably a 4-methylbenzhydrylamine resin, by activation with dicyclohexylcarbodiimide to yield a peptide with a C-terminal amide. Alternatively, a chloromethyl resin (Merrifield resin) may be used to yield a peptide with a free carboxylic acid at the C-terminal. After the last residue has been attached, the protected peptide-resin is treated with hydrogen fluoride to cleave the peptide from the resin, as well as deprotect the side chain functional groups. Crude product can be further purified by gel filtration, high pressure liquid chromatography (HPLC), partition chromatography, or ion-exchange chromatography.

If desired, and as outlined above, various groups may be introduced into the peptide of the composition during synthesis or during expression, which allow for linking to other molecules or to a surface. For example, cysteines can be used to make thioethers, histidines for linking to a metal ion complex, carboxyl groups for forming amides or esters, amino groups for forming amides, and the like.

The peptides may also be produced using cell-free translation systems. Standard translation systems, such as reticulocyte lysates and wheat germ extracts, use RNA as a template; whereas "coupled" and "linked" systems start with DNA templates, which are transcribed into RNA then translated.

Alternatively, the peptides may be produced by transfecting host cells with expression vectors that comprise a polynucleotide(s) that encodes one or more peptides. For recombinant production, a recombinant construct comprising a sequence which encodes one or more of the peptides is introduced into host cells by conventional methods such as calcium phosphate transfection, DEAE-dextran mediated transfection, microinjection, cationic lipid-mediated transfection, electroporation, transduction, scrape lading, ballistic introduction or infection.

One or more of the peptides may be expressed in suitable host cells, such as, for example, mammalian cells (for example, COS, CHO, BHK, 293 HEK, VERO, HeLa, HepG2, MDCK, W138, or NIH 3T3 cells), yeast (for example, *Saccharomyces* or *Pichia*), bacteria (for example, *E. coli, P. pastoris,* or *B. subtilis*), insect cells (for example, baculovirus in Sf9 cells) or other cells under the control of appropriate promoters using conventional techniques. Following transformation of the suitable host strain and growth of the host strain to an appropriate cell density, the cells are harvested by centrifugation, disrupted by physical or chemical means, and the resulting crude extract retained for further purification of the peptide or variant thereof.

Suitable expression vectors include, for example, chromosomal, non-chromosomal and synthetic polynucleotides, for example, derivatives of SV40, bacterial plasmids, phage DNAs, yeast plasmids, vectors derived from combinations of plasmids and phage DNAs, viral DNA such as vaccinia viruses, adenovirus, adeno-associated virus, lentivirus, canary pox virus, fowl pox virus, pseudorabies, baculovirus, herpes virus and retrovirus. The polynucleotide may be introduced into the expression vector by conventional procedures known in the art.

The polynucleotide which encodes one or more peptides may be operatively linked to an expression control sequence, i.e., a promoter, which directs mRNA synthesis. Representative examples of such promoters include the LTR or SV40 promoter, the *E. coli* lac or trp, the phage lambda PL promoter and other promoters known to control expression of genes in prokaryotic or eukaryotic cells or in viruses. The expression vector may also contain a ribosome binding site for translation initiation and a transcription terminator. The expression vectors may also include an origin of replication and a selectable marker, such as the ampicillin resistance gene of *E. coli* to permit selection of transformed cells, i.e., cells that are expressing the heterologous polynucleotide. The nucleic acid molecule encoding one or more of the peptides may be incorporated into the vector in frame with translation initiation and termination sequences.

One or more of the peptides can be recovered and purified from recombinant cell cultures (i.e., from the cells or culture medium) by well-known methods including ammonium sulphate or ethanol precipitation, acid extraction, anion or cation exchange chromatography, phosphocellulose chromatography, hydrophobic interaction chromatography, affinity chromatography, hydroxyapatite chromatography, lectin chromatography, and HPLC. Well known techniques for refolding proteins may be employed to regenerate active conformation when the peptide is denatured during isolation and or purification.

To produce a glycosylated peptide, it is preferred in some embodiments that recombinant techniques be used. To produce a glycosylated peptide, it is preferred in some embodiments that mammalian cells such as, COS-7 and Hep-G2 cells be employed in the recombinant techniques.

The peptides can also be prepared by cleavage of longer peptides, especially from food extracts.

Pharmaceutically acceptable salts of the peptides can be synthesised from the peptides which contain a basic or acid moiety by conventional chemical methods. Generally, the salts are prepared by reacting the free base or acid with stoichiometric amounts or with an excess of the desired salt-forming inorganic or organic acid or base in a suitable solvent.

Compositions, Vaccine Compositions, and Administration
Compositions and Vaccine Compositions The disclosure also provides a composition comprising a first peptide comprising the amino acid sequence ELQPFPQPELPYPQPQ (SEQ ID NO: 1), wherein the N-terminal glutamate is a pyroglutamate and the carboxyl group of the C-terminal glutamine is amidated; a second peptide comprising the amino acid sequence EQPFPQPEQPFPWQP (SEQ ID NO: 2), wherein the N-terminal glutamate is a pyroglutamate and the carboxyl group of the C-terminal proline is amidated; and a third peptide comprising the amino acid sequence EPEQPIPEQPQPYPQQ (SEQ ID NO: 3), wherein the N-terminal glutamate is a pyroglutamate and the carboxyl group of the C-terminal glutamine is amidated. In some embodiments, the composition is a vaccine composition.

The disclosure additionally provides a composition comprising a first peptide comprising the amino acid sequence PFPQPELPY (SEQ ID NO: 4) and the amino acid sequence PQPELPYPQ (SEQ ID NO: 5), optionally wherein the N-terminus comprises a pyroglutamate (e.g., any N-terminal glutamate is a pyroglutamate) and the C-terminus is amidated (e.g., any C-terminal glutamine is amidated); a second peptide comprising the amino acid sequence PFPQPEQPF (SEQ ID NO: 6) and the amino acid sequence PQPEQPFPW (SEQ ID NO: 7), optionally wherein the N-terminus comprises a pyroglutamate (e.g., any N-terminal glutamate is a pyroglutamate) and the C-terminus is amidated (e.g., any C-terminal proline is amidated); and a third peptide comprising the amino acid sequence EQPIPEQPQ (SEQ ID NO:

8) and the amino acid sequence PIPEQPQPY (SEQ ID NO: 9), optionally wherein the N-terminus comprises a pyroglutamate (e.g, any N-terminal glutamate is a pyroglutamate) and the C-terminus is amidated (e.g., any C-terminal proline is amidated). In some embodiments, the composition is a vaccine composition.

As used herein, the term "vaccine" refers to a composition comprising peptide(s) that can be administered to a subject having Celiac disease to modulate the subject's response to gluten. The vaccine may reduce the immunological reactivity of a subject towards gluten. Preferably, the vaccine induces tolerance to gluten.

Without being bound by any theory, administration of the vaccine composition to a subject may induce tolerance by clonal deletion of gluten-specific effector T cell populations, for example, gluten-specific CD4$^+$ T cells, or by inactivation (anergy) of said T cells such that they become less responsive, preferably, unresponsive to subsequent exposure to gluten (or peptides thereof). Deletion or inactivation of said T cells can be measured, for example, by contacting ex vivo a sample comprising said T cells with gluten or a peptide thereof and measuring the response of said T cells to the gluten or peptide thereof. An exemplary T cell response measurement is measurement of the level of interferon-gamma (IFN-$\gamma$, see, e.g., NCBI Gene ID 3458 and Protein ID NP_000610.2) in the sample after contact with the gluten or peptide thereof. A decreased level of IFN-$\gamma$ may indicate deletion or inactivation of said T cells. The level of IFN-$\gamma$ can be measured using any method known to those of skill in the art, e.g., using immuno-based detection methods such as Western blot or enzyme-linked immunosorbent assay (ELISA).

Alternatively, or in addition, administration of the vaccine composition may modify the cytokine secretion profile of the subject (for example, result in decreased IL-4, IL-2, TNF-$\alpha$, and/or IFN-$\gamma$, and/or increased IL-10). The vaccine composition may induce suppressor T cell subpopulations, for example Treg cells, to produce IL-10 and/or TGF-$\beta$ and thereby suppress gluten-specific effector T cells. The cytokine secretion profile of the subject can be measured using any method known to those of skill in the art, e.g., using immuno-based detection methods such as Western blot or enzyme-linked immunosorbent assay (ELISA).

The vaccine composition of the disclosure can be used for prophylactic treatment of a subject capable of developing Celiac disease and/or used in ongoing treatment of a subject who has Celiac disease. In some embodiments, the composition is for use in treating Celiac disease in a subject. In some embodiments, the subject is HLA-DQ2.5 positive. In some embodiments, the subject is HLA-DQ2.5 positive and HLA-DQ8 negative.

Effective Amount

The amount of a composition to be administered is referred to as the "effective amount". The term "effective amount" means the amount sufficient to provide the desired therapeutic or physiological effect when administered under appropriate or sufficient conditions. In some embodiments, the effective amount is 150 micrograms of the peptides provided herein (i.e., 50 micrograms of the first peptide and an equimolar amount of each of the second and third peptides). In some embodiments, the effective amount is 26.5 nmol of each of the first, second, and third peptides. Methods for producing equimolar peptide compositions are known in the art and provided herein (see, e.g., Example 1 and Muller et al. Successful immunotherapy with T-cell epitope peptides of bee venom phospholipase A2 induces specific T-cell anergy in patient allergic to bee venom. J. Allergy Clin. Immunol. Vol. 101, Number 6, Part 1: 747-754 (1998)). In some embodiments, the effective amount is 300 micrograms of the peptides provided herein (i.e., 100 micrograms of the first peptide and an equimolar amount of each of the second and third peptides). In some embodiments, this effective amount of the peptides is administered in sterile sodium chloride 0.9% USP as a bolus intradermal injection.

The effective amounts provided herein are believed to modify the T cell response, e.g., by inducing immune tolerance, to wheat, barley and rye in the subject, and preferably wheat, barley, rye and oats. Thus, a subject treated according to the disclosure preferably is able to eat at least wheat, rye, barley and optionally oats without a significant T cell response which would normally lead to clinical manifestations of active Celiac disease.

Pharmaceutically Acceptable Carriers

The composition may include a pharmaceutically acceptable carrier. The term "pharmaceutically acceptable carrier" refers to molecular entities and compositions that do not produce an allergic, toxic or otherwise adverse reaction when administered to a subject, particularly a mammal, and more particularly a human. The pharmaceutically acceptable carrier may be solid or liquid. Useful examples of pharmaceutically acceptable carriers include, but are not limited to, diluents, excipients, solvents, surfactants, suspending agents, buffering agents, lubricating agents, adjuvants, vehicles, emulsifiers, absorbants, dispersion media, coatings, stabilizers, protective colloids, adhesives, thickeners, thixotropic agents, penetration agents, sequestering agents, isotonic and absorption delaying agents that do not affect the activity of the active agents of the disclosure. In some embodiments, the pharmaceutically acceptable carrier is a sodium chloride solution (e.g., sodium chloride 0.9% USP).

The carrier can be any of those conventionally used and is limited only by chemico-physical considerations, such as solubility and lack of reactivity with the active agent, and by the route of administration. Suitable carriers for this disclosure include those conventionally used, for example, water, saline, aqueous dextrose, lactose, Ringer's solution, a buffered solution, hyaluronan, glycols, starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like. Liposomes may also be used as carriers.

Techniques for preparing pharmaceutical compositions are generally known in the art as exemplified by Remington's Pharmaceutical Sciences, 16th Ed. Mack Publishing Company, 1980.

Administration preferably is intradermal administration. Thus, the composition of the disclosure may be in a form suitable for intradermal injection. In some embodiments, the composition of the disclosure is in the form of a bolus for intradermal injection.

Injectables

The pharmaceutical composition(s) may be in the form of a sterile injectable aqueous or oleagenous suspension. In some embodiments, the composition is formulated as a sterile, injectable solution. This suspension or solution may be formulated according to known methods using those suitable dispersing or wetting agents and suspending agents which have been mentioned above. The sterile injectable preparation may be a suspension in a non-toxic parenterally-acceptable diluent or solvent, for example as a solution in 1,3-butanediol. Among the acceptable carriers that may be employed are water, Ringer's solution and isotonic sodium chloride solution. In some embodiments, the composition is formulated as a sterile, injectable solution, wherein the solution is a sodium chloride solution (e.g., sodium chloride 0.9% USP). In some embodiments, the composition is formulated as a bolus for intradermal injection.

Examples of appropriate delivery mechanisms for intradermal administration include, but are not limited to, implants, depots, needles, capsules, and osmotic pumps.

Dosage

It is especially advantageous to formulate the active in a dosage unit form for ease of administration and uniformity of dosage. "Dosage unit form" as used herein refers to physically discrete units suited as unitary dosages for the subject to be treated; each unit containing a predetermined quantity of active agent calculated to produce the desired therapeutic effect in association with the required pharmaceutical carrier. The specification for the dosage unit forms are dictated by and directly dependent on the unique characteristics of the active agent and the particular therapeutic effect to be achieved, and the limitations inherent in the art of compounding such an active agent for the treatment of subjects. Examples of dosage units include sealed ampoules and vials and may be stored in a freeze-dried condition requiring only the addition of the sterile liquid carrier immediately prior to use.

The composition may also be included in a container, pack, or dispenser together with instructions for administration.

The actual amount administered (or dose or dosage) and the rate and time-course of administration are as provided herein.

The administration may occur at least once, e.g., once or twice a week. In some embodiments, a composition described herein is administered once or twice a week. In some embodiments, a composition described herein is administered for 3, 4 or 8 weeks. In some embodiments, a composition described herein is administered once a week for 8 weeks. In some embodiments, a composition described herein is administered once a week for 3 weeks. In some embodiments, a composition described herein is administered twice a week for 4 weeks. In some embodiments, a composition described herein is administered twice a week for 8 weeks. In some embodiments, the administration occurs 3, 8 or 16 times.

Kits

Another aspect of the disclosure relates to kits. In some embodiments, the kit comprises a composition comprising the peptides as described herein. The peptides can be contained within the same container or separate containers. In some embodiments, the kit can further comprise a placebo. In some embodiments, the peptide or peptides may be contained within the container(s) (e.g., dried onto the wall of the container(s)). In some embodiments, the peptides are contained within a solution separate from the container, such that the peptides may be added to the container at a subsequent time. In some embodiments, the peptides are in lyophilized form in a separate container, such that the peptides may be reconstituted and added to the container at a subsequent time.

In some embodiments, the kit further comprises instructions for reconstitution, mixing, administration, etc. In some embodiments, the instructions include the methods described herein. Instructions can be in any suitable form, e.g., as a printed insert or a label.

Methods of Treatment

Aspects of the disclosure relate to use of the compositions described herein for treating a subject having, suspected of having or at risk of having Celiac disease.

As used herein, the terms "treat", "treating", and "treatment" include abrogating, inhibiting, slowing, or reversing the progression of a disease or condition, or ameliorating or preventing a clinical symptom of the disease (for example, Celiac disease). Treatment may include induction of immune tolerance (for example, to gluten or peptide(s) thereof), modification of the cytokine secretion profile of the subject and/or induction of suppressor T cell subpopulations to secrete cytokines. Thus, a subject treated according to the disclosure preferably is able to eat at least wheat, rye, barley and optionally oats without a significant T cell response which would normally lead to symptoms of Celiac disease.

Identifying Subjects for Treatment

In some embodiments, methods described herein comprise treating a subject who has Celiac disease. Thus, it may be desirable to identify subjects, such as subjects with Celiac disease, who are likely to benefit from administration of a composition described herein. In any one of the methods provided, the method may comprise a step of identifying a subject likely to benefit from such administration. Any diagnostic method or combinations thereof for Celiac disease is contemplated for identifying such a subject. Exemplary methods include, but is not limited to, intestinal biopsy, serology (measuring the levels of one or more antibodies present in the serum), and genotyping (see, e.g., Husby S, Koletzko S, Korponay-Szabo I R, Mearin M L, Phillips A, Shamir R, Troncone R, Giersiepen K, Branski D, Catassi C et al: European Society for Pediatric Gastroenterology, Hepatology, and Nutrition guidelines for the diagnosis of coeliac disease. J Pediatr Gastroenterol Nutr 2012, 54(1):136-160. AND/OR Rubio-Tapia A, Hill I D, Kelly C P, Calderwood A H, Murray J A. ACG clinical guidelines: diagnosis and management of celiac disease. Am J Gastroenterol 2013; 108:656-76. AND/OR Ludvigsson J F, Leffler D A, Bai J C, Biagi F, Fasano A, Green P H, Hadjivassiliou M, Kaukinen K, Kelly C P, Leonard J N, Lundin K E, Murray J A, Sanders D S, Walker M M, Zingone F, Ciacci C. The Oslo definitions for coeliac disease and related terms. Gut 2012; 62:43-52.).

The presence of serum antibodies can be detected using methods known to those of skill in the art, e.g., by ELISA, histology, cytology, immunofluorescence or western blotting. Such antibodies include, but are not limited to: IgA anti-endomysial antibody (IgA EMA), IgA anti-tissue transglutaminase 2 antibody (IgA tTG), IgA anti-deamidated gliadin peptide antibody (IgA DGP), and IgG anti-deamidated gliadin peptide antibody (IgG DGP). Deamidated gliadin peptide-IgA (DGP-IgA) and deamidated gliadin peptide-IgG (DGP-IgG) can be evaluated with commercial kits (e.g. INV 708760, 704525, and 704520, INOVA Diagnostics, San Diego, Calif.).

Subjects can be tested for the presence of the HLA-DQA and HLA-DQB susceptibility alleles encoding HLA-DQ2.5 (DQA1*05 and DQB1*02), DQ2.2 (DQA1*02 and DQB1*02) or DQ8 (DQA1*03 and DQB1*0302). Exemplary sequences that encode the DQA and DQB susceptibility alleles include HLA-DQA1*0501 (Genbank accession number: AF515813.1) HLA-DQA1*0505 (AH013295.2), HLA-DQB1*0201 (AY375842.1) or HLA-DQB1*0202 (AY375844.1). Methods of genetic testing are well known in the art (see, e.g., Bunce M, et al. Phototyping: comprehensive DNA typing for HLA-A, B, C, DRB1, DRB3, DRB4, DRB5 & DQB1 by PCR with 144 primer mixes utilizing sequence-specific primers (PCR-SSP). Tissue Antigens 46, 355-367 (1995); Olerup O, Aldener A, Fogdell A. HLA-DQB1 and DQA1 typing by PCR amplification with sequence-specific primers in 2 hours. Tissue antigens 41, 119-134 (1993); Mullighan C G, Bunce M, Welsh K I. High-resolution HLA-DQB1 typing using the polymerase chain reaction and sequence-specific primers. Tissue-Antigens. 50, 688-92 (1997); Koskinen L, Romanos J, Kaukinen K, Mustalahti K, Korponay-Szabo I, et al. (2009) Cost-effective HLA typing with tagging SNPs predicts celiac disease risk haplotypes in the Finnish, Hungarian, and Italian populations. Immunogenetics 61: 247-256; and Monsuur A J, de Bakker P I, Zhernakova A, Pinto D, Verduijn W, et al. (2008) Effective detection of human leukocyte antigen risk alleles in celiac disease using tag single nucleotide polymorphisms. PLoS ONE 3: e2270). Subjects that have one or more copies of a susceptibility allele are considered to be positive for that allele. Detection of the presence of susceptibility alleles can be accomplished by any nucleic acid assay known in the art, e.g., by polymerase chain reaction (PCR) amplification of DNA extracted from the patient followed by hybridization with sequence-specific oligonucleotide probes or using leukocyte-derived DNA (Koskinen L, Romanos J, Kaukinen K, Mustalahti K, Korponay-Szabo I, Barisani D, Bardella M T, Ziberna F, Vatta S, Szeles G et al: Cost-effective HLA typing with tagging SNPs predicts Celiac disease risk haplotypes in the Finnish, Hungarian, and Italian populations. Immunogenetics 2009, 61(4):247-256; Monsuur A J, de Bakker P I, Zhernakova A, Pinto D, Verduijn W, Romanos J, Auricchio R, Lopez A, van Heel D A, Crusius J B et al: Effective detection of human leukocyte antigen risk alleles in Celiac disease using tag single nucleotide polymorphisms. PLoS ONE 2008, 3(5): e2270).

EXAMPLES

Example 1: Preparation of a 150 Microgram Dosage Composition of the First, Second, and Third Peptide A dose of 150 μg the peptide composition was defined by there being 50 μg (26.5 nmol) of pure peptide 1, and an equimolar amount of peptide 2 and peptide 3. The molar equivalent of 50 μg peptide 1 was given by 50 μg/1889.3 g/mol=26.5 nmol. When preparing a solution containing 150 μg of the peptide composition, for the constituent peptides, the weight of each peptide was adjusted according to peptide purity and peptide content of the lyophilized stock material. For example, if the peptide 1 stock material had peptide purity of 98% and its peptide content was 90%, the weight of stock material yielding 50 μg peptide 1 was 50 μg/ (peptide purity×peptide content)=50 ug/(0.98×0.90)=56.7 ug.

The molar amount of peptide 1 in 150 μg of the peptide composition was 26.5 nmol, and the weight of lyophilized peptide 2 stock material was therefore given by 26.5 nmol× 1833.2 g/mol/(peptide purity×peptide content). For example, if peptide 2 peptide purity was 99%, and peptide content of 95%, the mass of stock required was 51.7 ug.

The molar amount of peptide 3 in 150 ug of the peptide composition was 26.5 nmol, and the weight of lyophilized peptide 3 stock material was therefore given by 26.5 nmol× 1886.2 g/mol/(peptide purity×peptide content). For example, if peptide 3 peptide purity was 98%, and peptide content of 92%, the mass of stock required was 55.4 ug.

Example 2: A Phase I Randomized, Double-Blind, Placebo-Controlled, Multiple Ascending Dose Study in Patients with Celiac Disease Primary Objective:
  To determine the safety and tolerability of an equimolar composition of peptides comprising SEQ ID NOs: 1, 2, and 3 (each peptide comprising an N-terminal pyroglutamate and C-terminal amidated amino acid) when administered intradermally to human leukocyte antigen (HLA)-DQ2.5+ patients with Celiac disease on a gluten-free diet (GFD) (patient has HLA-DQ2.5 genotype (both HLA-DQA1*05 and HLA-DQB 1*02, homozygous or heterozygous) but does not possesses the genes encoding HLA DQ8 (either HLA-DQA1*03 or HLA-DQB1*0302))

Secondary Objectives:
  To assess the pharmacokinetics (PK) of the equimolar composition when administered intradermally to patients with Celiac disease on a gluten-free diet (GFD)
  To assess the effect of the equimolar composition on the immunological response and on clinical tolerance to gluten when administered intradermally to patients with Celiac disease on a GFD Exploratory Objective:
  To assess the effect of the equimolar composition on small bowel mucosal histology in patients with Celiac disease on a GFD Study Design:
  The study included a dose treatment cohort (150 μg per dose, i.e., 50 micrograms of the first peptide and an equimolar amount of each of the second and third peptides) that received the composition provided herein or placebo given intradermally on a twice weekly schedule for eight weeks in a 2:1 ratio.

Drug, Dosage, and Route of Administration:
  The composition was an equimolar mixture of three peptides.
  The composition dose: 150 μg
  Placebo: Sodium chloride 0.9% USP (same as vehicle/diluent for the composition)
  Dose frequency: twice weekly
  Route of administration: intradermal injection
  All study injections were prepared by an unblinded pharmacist at the study center while remaining double-blind to the patient and investigator.

Safety Assessments:
  A medical history, physical examination, vital sign measurements, ECG, and laboratory assessment (including hematology, biochemistry, and urinalysis) occurred at certain time points.
  Adverse events (AE) and concomitant medications were assessed at each visit.
  A daily gastrointestinal (GI) symptom diary and weekly gastrointestinal symptom rating scale (GSRS) were used to record gastrointestinal symptoms throughout the trial.
  Cytokine, chemokine, and T-cell measurements were assessed.
  Presence of antitherapeutic antibodies were assessed.
  An independent data safety monitoring board (DSMB), whose charter was documented prior to randomization of the first patient, assessed the progress of the clinical trial, including the safety data, and recommended whether to continue, modify, or stop the trial at any time.

Pharmacokinetic Assessments:
  For each cohort, serial blood samples were collected for assessment of pharmacokinetics.

Pharmacodynamic Assessments:
  Specific immune responses were assessed throughout the trial.

Exploratory Assessment:

An upper endoscopy and small bowel biopsy for histological assessment was performed on patients in the biopsy cohort at screening and following the last dose of the composition.

Statistical Methods:

No formal hypothesis testing was performed. Data were summarized appropriately and all data were listed. Adverse events (AE) were summarized, presenting the numbers and percent of patients having any AE and having AEs in each system organ class and preferred term.

Example 3: Results of the Phase I Randomized, Double-Blind, Placebo-Controlled, Multiple Ascending Dose Study in Patients with Celiac Disease 3 cohorts of subjects with HLA-DQ2.5+ biopsy-proven Celiac disease on a gluten-free diet for at least 1 year were included in the study. The first cohort (Cohort 1) contained 12 subjects who were dosed with 150 mcg of a peptide composition (an equimolar composition in sodium chloride 0.9% USP of 3 peptides, peptide 1, peptide 2, and peptide 3, comprising SEQ ID NOs: 1, 2, and 3, respectively, each peptide comprising an N-terminal pyroglutamate and C-terminal amidated amino acid) or a placebo (sodium chloride 0.9% USP) intradermally, twice a week for 8 weeks total.

The second cohort (Cohort 2) contained 12 subjects who were dosed with 300 mcg of the peptide composition or the placebo intradermally, twice a week for 8 weeks total. The peptide composition to placebo ratio for each of Cohorts 1 and 2 were 2:1. Both Cohorts 1 and 2 received an oral gluten challenge and were assessed for gamma-interferon (gIFN) release and then returned to baseline prior to starting the treatment regimen. The third cohort (Cohort 7) contained 14 subjects who were dosed with 150 mcg of the peptide composition or the placebo intradermally, twice a week for 8 weeks total. The peptide composition to placebo ratio for Cohort 7 was 1:1. The subjects in Cohort 7 did not undergo an oral gluten challenge or a gIFN release assay before starting the dosage regimen.

The progress of each subject before, during and after the trial was assessed using multiple tests including serology (tTG-IgA, DGP-IgG, DGP-IgA, and EMA-IgA), histology, and IFNg whole blood release assay, and cytokine/chemokines in plasma (measured by MAGPIX® multiplex platform).

Subject disposition is summarized in Table 1.

TABLE 1

Subject disposition.

| Completion Status | Cohort 1 (150 mg) (N = 8) | Cohort 2 (300 mg) (N = 8) | Cohort 7 (150 mg) (N = 7) | Placebo (from Cohorts 1 and 2) (N = 7) | Placebo (from Cohort 7) (N = 7) | All Subjects Dosed (N = 39) | All Subjects Screened (N = 67) |
|---|---|---|---|---|---|---|---|
| Screened | | | | | | | 67 (100%) |
| Enrolled | 8 (100%) | 10 (100%) | 7 (100%) | 7 (100%) | 7 (100%) | 39 (100%) | 39 (58%) |
| Completed the study as required | 8 (100%) | 6 (60%) | 7 (100%) | 6 (86%) | 7 (100%) | 34 (87%) | |
| Completed study treatment per protocol (received at least 15 of 16 doses) | 8 (100%) | 2 (20%) | 7 (100%) | 5 (71%) | 7 (100%) | 29 (74%) | |
| Received all 16 doses of study treatment | 7 (88%) | 2 (20%) | 5 (71%) | 4 (57%) | 6 (86%) | 24 (62%) | |
| Discontinued the study prior to completion | | 8 (80%) | | 2 (29%) | | 10 (26%) | |

Subject demographics are summarized in Table 2. The extent of exposure for each subject is summarized in Table 3.

TABLE 2

Subject Demographics

| Parameter | Statistic | Cohort 1 (150 mg) (N = 8) | Cohort 2 (300 mg) (N = 10) | Cohort 7 (150 mg) (N = 7) | Placebo (pooled) (N = 14) | All subjects dosed (N = 39) |
|---|---|---|---|---|---|---|
| Age (years) | N | 8 | 10 | 7 | 14 | 39 |
| | Mean | 52.0 | 50.0 | 42.6 | 39.1 | 45.2 |
| | SD | 11.9 | 10.1 | 5.4 | 15.5 | 13.0 |
| | Median | 52.5 | 52.0 | 45.0 | 34.0 | 47.0 |
| | Min | 31 | 28 | 33 | 18 | 18 |
| | Max | 66 | 64 | 47 | 64 | 66 |

TABLE 2-continued

Subject Demographics

| Parameter | Statistic | Cohort 1 (150 mg) (N = 8) | Cohort 2 (300 mg) (N = 10) | Cohort 7 (150 mg) (N = 7) | Placebo (pooled) (N = 14) | All subjects dosed (N = 39) |
|---|---|---|---|---|---|---|
| Race | | | | | | |
| White | n (%) | 8 | 10 | 7 | 14 | 39 (100%) |
| Sex | | | | | | |
| Female | n (%) | 7 | 7 | 5 | 10 | 29 (74%) |
| Male | n (%) | 1 | 3 | 2 | 4 | 10 (26%) |
| Height | N | 8 | 10 | 7 | 14 | 39 |
| (cm) | Mean | 167.7 | 170.1 | 168.4 | 170.6 | 169.5 |
| | SD | 10.0 | 9.8 | 8.3 | 10.0 | 9.4 |
| | Median | 168.7 | 167.0 | 173.0 | 170.5 | 169.0 |
| | Min | 154 | 158 | 156 | 156 | 154 |
| | Max | 186 | 186 | 179 | 186 | 186 |
| Weight | N | 8 | 10 | 7 | 14 | 39 |
| (kg) | Mean | 70.66 | 85.34 | 74.40 | 66.55 | 73.62 |
| | SD | 11.17 | 13.02 | 11.58 | 12.91 | 14.07 |
| | Median | 69.20 | 85.05 | 73.00 | 64.10 | 70.50 |
| | Min | 60.2 | 66.0 | 58.5 | 48.5 | 48.5 |
| | Max | 95.1 | 105.5 | 92.5 | 92.3 | 105.5 |
| BMI | N | 8 | 10 | 7 | 14 | 39 |
| (kg/m^2) | Mean | 25.24 | 29.55 | 26.13 | 22.81 | 25.63 |
| | SD | 4.28 | 4.54 | 2.63 | 3.72 | 4.60 |
| | Median | 23.91 | 28.91 | 25.23 | 22.64 | 25.23 |
| | Min | 20.7 | 25.2 | 23.3 | 17.2 | 17.2 |
| | Max | 33.2 | 40.2 | 30.9 | 32.3 | 40.2 |

TABLE 3

Summary of subject exposure

| Cohort | Treatment | Dose level | Number of Doses | Total Dose | Number of Subjects |
|---|---|---|---|---|---|
| 1 | peptide composition | 150 | 16 | 2400 | 7 |
| 1 | peptide composition | 150 | 15 | 2250 | 1 |
| 1 | Placebo | 0 | 16 | 0 | 4 |
| 2 | peptide composition | 300 | 16 | 4800 | 2 |
| 2 | peptide composition | 300 | 5 | 1500 | 1 |
| 2 | peptide composition | 300 | 4 | 1200 | 2 |
| 2 | peptide composition | 300 | 3 | 900 | 1 |
| 2 | peptide composition | 300 | 2 | 600 | 1 |
| 2 | peptide composition | 300 | 1 | 300 | 3 |
| 2 | Placebo | 0 | 15 | 0 | 1 |
| 2 | Placebo | 0 | 10 | 0 | 1 |
| 2 | Placebo | 0 | 5 | 0 | 1 |
| 7 | peptide composition | 150 | 16 | 2400 | 5 |
| 7 | peptide composition | 150 | 15 | 2250 | 2 |
| 7 | Placebo | 0 | 16 | 0 | 6 |
| 7 | Placebo | 0 | 15 | 0 | 1 |

Immune Tolerance

Immune tolerance induced by the peptide composition was measured using two types of assays: gIFN release to gluten and cytokine/chemokine plasma assays.

An ex vivo whole blood cytokine release assay was performed pre- and post-treatment with the peptide composition. Blood was collected 6 days after commencing 3-day oral challenge with gluten (approximately 9 g/day). The MAGPIX® assay was used to confirm elevated IFN-γ plasma levels in blood incubated with the three constituent peptides present in the peptide composition (0.05 mg/mL/peptide), and also to show that levels of interleukin-2 and IFN-γ-inducible protein (IP-10) correlated with elevated concentrations of IFN-γ. Pretreatment gluten challenge was 4-5 weeks prior to commencing dosing with the peptide composition. Post-treatment 3-day gluten challenge was commenced the day after last dose of the peptide composition.

Subjects were determined to be responsive to gluten if the subject had detectable gIFN released after gluten challenge before the first dose of the peptide composition. By this criteria, 7 of 8 subjects at 150 mcg and 3 of 4 subjects at 300 mcg were responsive to gluten. Subjects were then determined to be tolerant to gluten after the last dose of the peptide composition if the subject had significantly less gIFN released after the second gluten challenge after the last dose of the peptide composition. By this criteria 5 of 7 subjects at 150 mcg and 1 of 1 at 300 mcg originally responsive to gluten were tolerant to gluten after treatment (2 of the 300 mcg subjects did not finish the treatment and were not included in the tolerance analysis).

This assessment was also performed using a level of 7.2 pg/mL of IFN-γ in the cytokine release assay as a cut-off level for reactivity v. non-reactivity to the peptide composition. As shown in FIG. 5, most subjects that were reactive to the peptides before treatment (see pre-treatment column in FIG. 5) became non-reactive to the peptides after treatment (see post-treatment column in FIG. 5), indicating that treatment induced immune tolerance to the peptides.

The second measure of immune tolerance was a plasma cytokine/chemokine assay. Plasma cytokines and chemokines were measured at several timepoints pre and post first and last dose (visits 6 and 21). For a subject to be responsive they needed to have a greater than 2 fold increase after the first dose for IL-8 and MCP-1. For a subject to be tolerant they had to have less than 2 fold increase after the last dose for IL-8 and MCP-1. By this criteria, 8 of 8 subjects in Cohort 1 (150 micrograms), and 3 of 4 subjects in Cohort 2 (300 micrograms) and 6 of 7 in Cohort 7 (150 micrograms) were responsive to the first dose. Of the responsive subjects, 8 of 8, 1 of 1 and 6 of 6 were tolerant in the three cohorts, respectively. These results indicate that immune tolerance to gluten and to the peptide composition was induced in several subjects treated with the peptide composition. The assay results for an exemplary subject from Cohort 1 (150 micrograms the peptide composition) who was both responsive and tolerant to gluten and the peptide composition are shown in Table 4.

TABLE 4

Tolerance Assay results for representative subject from Cohort 1 (tolerant to both gluten and the peptide composition)

| Assay Measurement | Visit 6 (First dose) | Visit 21 (last dose) |
|---|---|---|
| GI symptoms | 18 | 6 |
| gIFN release, fold increase | 345 | 0.31 |
| gIFN, pg/mL | 3,461 | −4.6 |
| IL-2, fold increase | 10 | 1 |
| IL-8, fold increase | 20 | 0.9 |
| IL-10, fold increase | 8.4 | 0.75 |

TABLE 4-continued

Tolerance Assay results for representative subject from Cohort 1 (tolerant to both gluten and the peptide composition)

| Assay Measurement | Visit 6 (First dose) | Visit 21 (last dose) |
|---|---|---|
| MCP-1, fold increase | 18 | 1.06 |
| Peptide 1, pharmacokinetics | 1.67 | 1.48 |

Other Parameters of the Study

Figure 2:
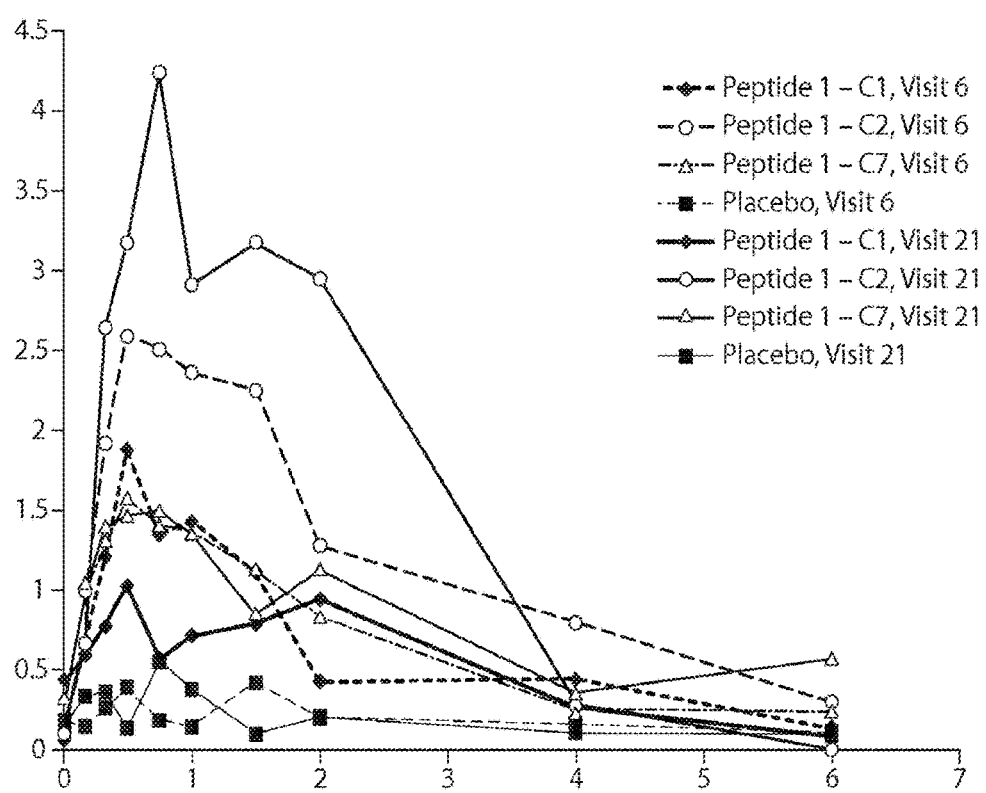
FIG. 2 is a graph showing the pharmacokinetics of peptide 1 (SEQ ID NO: 1, with an N-terminal pyroglutamate and a C-terminal amide group). The x-axis is time in hours after the dose. The y-axis is log(plasma concentration).
Figure 3:
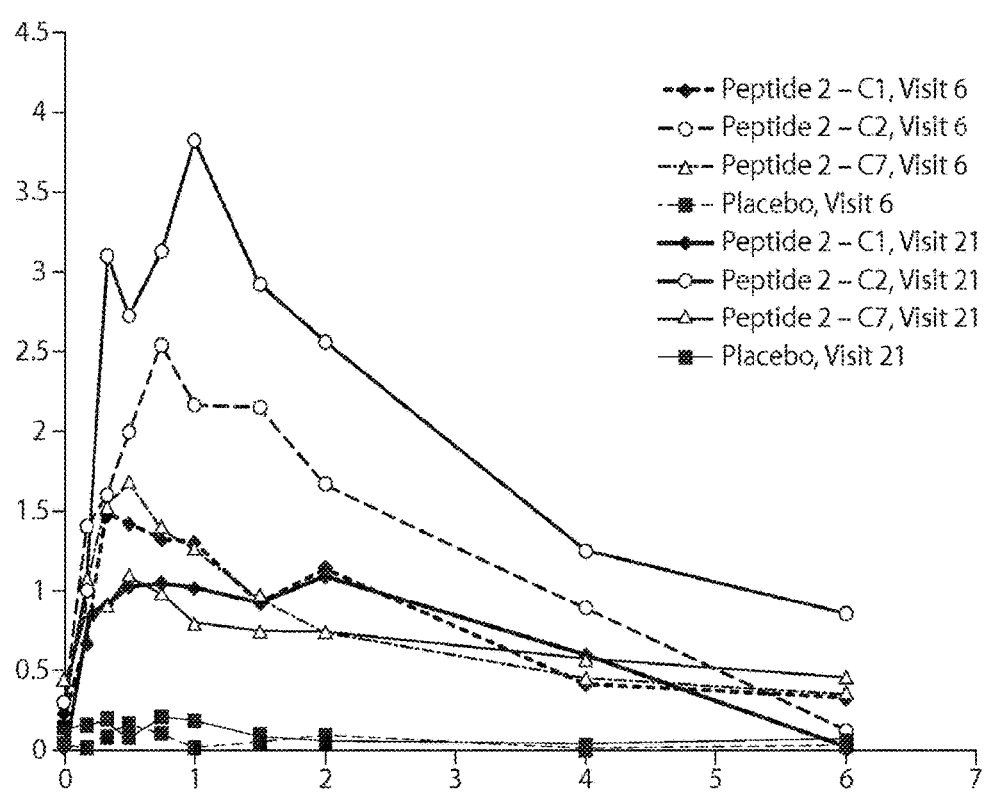
FIG. 3 is a graph showing the pharmacokinetics of peptide 2 (SEQ ID NO: 2, with an N-terminal pyroglutamate and a C-terminal amide group). The x-axis is time in hours after the dose. The y-axis is log(plasma concentration).
Figure 4:
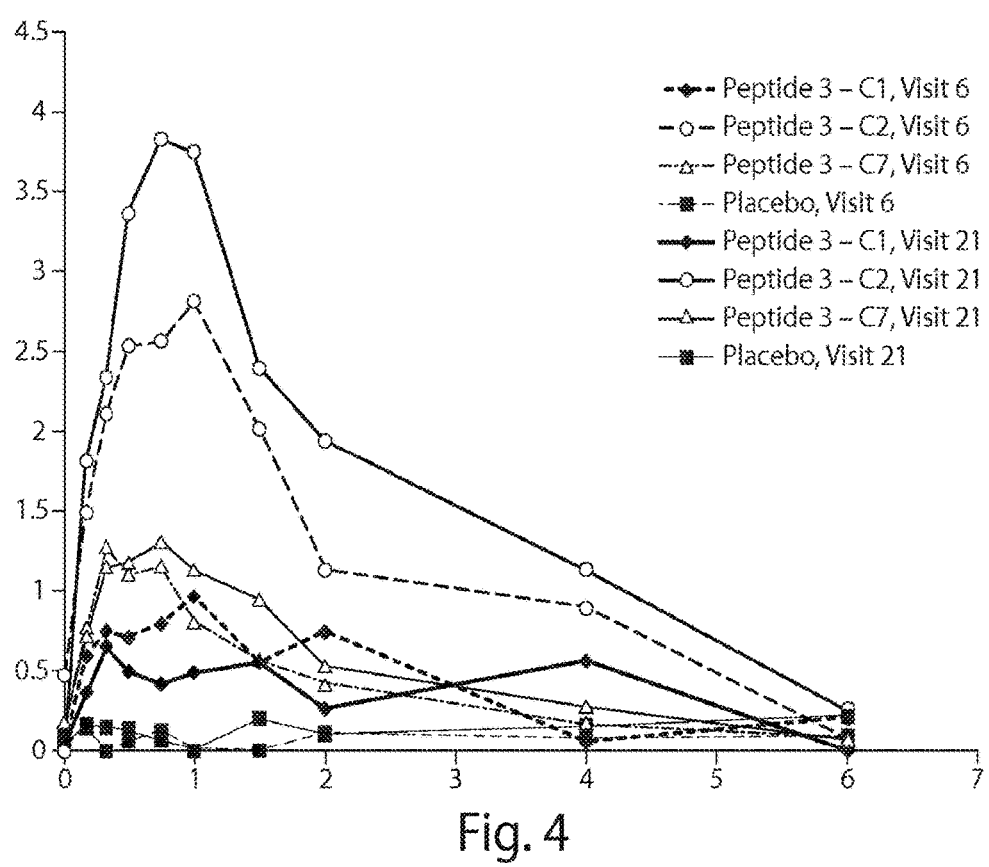
FIG. 4 is a graph showing the pharmacokinetics of peptide 3 (SEQ ID NO: 3, with an N-terminal pyroglutamate and a C-terminal amide group). The x-axis is time in hours after the dose. The y-axis is log(plasma concentration).

Lymphocyte subpopulations were analyzed to identify whether there was systemic changes during treatment with the peptide composition. FACS analysis showed that there was no change in CD4+, CD8+, NK or B-cell compartments as expected for antigen-specific immunotherapy. There were some fluctuations noted in CD19, CD56 cells. AntiTherapeutic Antibodies (ATA, also called anti-drug antibodies, ADA) were not detected in any subjects. There was no difference between the pharmacokinetics of the peptides at the first and last dose (FIGS. 2-4). The lack of activation of peptide composition-specific B-cells was consistent with the PK showing no change between the first and last dose. No subjects converted from baseline negative to positive after therapy as measured using standard serology (tissue-transglutaminase-IgA (tTG-IgA), anti-deamidated gliadin peptide-IgG or IgA (DGP-IgG, DGP-IgA), and anti-endomysial-IgA (EMA-IgA)). The biopsy Modified Marsh Scores for the treatment vs. placebo group are shown in Tables 5 and 6.

TABLE 5

Biopsy Modified Marsh Scores - treated

| | Pre-treatment scores | | | | Post-treatment scores | | | |
|---|---|---|---|---|---|---|---|---|
| | Bulb + Part 1 | Part 2 + Part 3 | Bulb + Parts 1, 2, 3 | (Parts 2, 3) − (Bulb + Part 1) | Bulb + Part 1 | Part 2 + Part 3 | Bulb + Parts 1, 2, 3 | (Parts 2, 3) − (Bulb + Part 1) |
| Subject Number | | | | | | | | |
| 1 | 0 | 0 | 0 | 0 | 0 | 0 | 0 | 0 |
| 2 | 0 | 0 | 0 | 0 | 0 | 0 | 0 | 0 |
| 3 | 0 | 0 | 0 | 0 | 0 | 0 | 0 | 0 |
| 4 | 0 | 0 | 0 | 0 | 0 | 0 | 0 | 0 |
| 5 | 5 | 13 | 18 | 8 | 10 | 13 | 23 | 3 |
| 6 | 1 | 2 | 3 | 1 | 4 | 4 | 8 | 0 |
| 7 | 6 | 3 | 9 | −3 | 4 | 2 | 6 | −2 |
| Parameters | | | | | | | | |
| N | 7 | 7 | 7 | 7 | 7 | 7 | 7 | 7 |
| Mean | 1.7 | 2.6 | 4.3 | 0.9 | 2.6 | 2.7 | 5.3 | 0.1 |
| Std Dev | 2.6 | 4.8 | 6.9 | 3.4 | 3.8 | 4.8 | 8.5 | 1.5 |
| Median | 0 | 0 | 0 | 0 | 0 | 0 | 0 | 0 |
| Min | 0 | 0 | 0 | −3 | 0 | 0 | 0 | −2 |
| Max | 6 | 13 | 18 | 8 | 10 | 13 | 23 | 3 |
| p-value | | | | 0.750 | | | | 1.000 |

TABLE 6

Biopsy Modified Marsh Scores - Placebo

| | Pre-treatment scores | | | | Post-treatment scores | | | |
|---|---|---|---|---|---|---|---|---|
| | Bulb + Part 1 | Part 2 + Part 3 | Bulb + Parts 1, 2, 3 | (Parts 2, 3) − (Bulb + Part 1) | Bulb + Part 1 | Part 2 + Part 3 | Bulb + Parts 1, 2, 3 | (Parts 2, 3) − (Bulb + Part 1) |
| Subject Number | | | | | | | | |
| 1 | 0 | 0 | 0 | 0 | 2 | 1 | 3 | −1 |
| 2 | 0 | 0 | 0 | 0 | 0 | 0 | 0 | 0 |
| 3 | 0 | 0 | 0 | 0 | 0 | 0 | 0 | 0 |

TABLE 6-continued

Biopsy Modified Marsh Scores - Placebo

| | Pre-treatment scores | | | | Post-treatment scores | | | |
|---|---|---|---|---|---|---|---|---|
| | Bulb + Part 1 | Part 2 + Part 3 | Bulb + Parts 1, 2, 3 | (Parts 2, 3) − (Bulb + Part 1) | Bulb + Part 1 | Part 2 + Part 3 | Bulb + Parts 1, 2, 3 | (Parts 2, 3) − (Bulb + Part 1) |
| 4 | 0 | 0 | 0 | 0 | 0 | 0 | 0 | 0 |
| 5 | 0 | 0 | 0 | 0 | 4 | 0 | 4 | −4 |
| 6 | 0 | 0 | 0 | 0 | 0 | 0 | 0 | 0 |
| 7 | 2 | 1 | 3 | −1 | 7 | 11 | 18 | 4 |
| Parameters | | | | | | | | |
| N | 7 | 7 | 7 | 7 | 7 | 7 | 7 | 7 |
| Mean | 0.3 | 0.1 | 0.4 | −0.1 | 1.9 | 1.7 | 3.6 | −0.1 |
| Std Dev | 0.8 | 0.4 | 1.1 | 0.4 | 2.7 | 4.1 | 6.6 | 2.3 |
| Median | 0 | 0 | 0 | 0 | 0 | 0 | 0 | 0 |
| Min | 0 | 0 | 0 | −1 | 0 | 0 | 0 | −4 |
| Max | 2 | 1 | 3 | 0 | 7 | 11 | 18 | 4 |
| p-value | | | | 1.000 | | | | 1.000 |

Adverse Events

Treatment emergent adverse events are summarized in Tables 7-9. The adverse events were mainly gastrointestinal symptoms and headaches, and were worse early on in the study. The GI adverse events recapitulated oral gluten exposure symptoms. Generally, adverse events occurred about 2 hours post dosing and resolved within 24 hours. Adverse events were primarily noted in week 1 of dosing. Adverse events were more severe in Cohort 1 (150 mg with oral challenge) than in Cohort 7 (150 mg without oral challenge). Interestingly, the gastrointestinal symptoms were worse on active drug vs. placebo early in the study but not late in study. The adverse events that occurred after the last dose (dose 16) were similar to placebo. Three subjects from Cohort 2 (300 micrograms) were withdrawn from the study due to gastrointestinal-related adverse events.

TABLE 7

Treatment emergent adverse events (TEAEs)

| | Cohort 1 (150 mg) (N = 8) | Cohort 2 (300 mg) (N = 10) | Cohort 7 (150 mg) (N = 7) | Placebo (from Cohorts 1 and 2) (N = 7) | Placebo (Cohort 7) (N = 7) | All Subjects Dosed (N = 39) |
|---|---|---|---|---|---|---|
| Number of Subjects with TEAEs | 7 (88%) | 10 (100%) | 6 (86%) | 5 (71%) | 7 (100%) | 35 (90%) |
| Number of Subjects with Study Drug Related TEAEs | 6 (75%) | 9 (90%) | 4 (57%) | 3 (43%) | 3 (43%) | 25 (64%) |
| Number of Subjects with Moderate or Severe TEAEs | 6 (75%) | 8 (80%) | 3 (43%) | 2 (29%) | | 19 (49%) |
| Number of Subjects with Study Drug Related, Moderate or Severe TEAEs | 5 (63%) | 8 (80%) | 1 (14%) | | | 14 (36%) |
| Number of Subjects with SAE | | 1 (10%) | | | | 1 (3%) |
| Number of Treatment-Emergent Adverse Events | 26 | 26 | 22 | 14 | 27 | 115 |
| Number of Study Drug Related TEAEs | 17 | 16 | 7 | 5 | 5 | 50 |
| Number of Moderate or Severe TEAEs | 11 | 12 | 4 | 2 | | 29 |
| Number of Study Drug Related, Moderate or Severe TEAEs | 7 | 8 | 2 | | | 17 |
| Number of SAEs | | 1 | | | | 1 |

TABLE 8

AEs by Severity and System Organ Class

| System Organ Class, Preferred term | Severity | Cohort 1 (150 mg) (N = 8) | Cohort 2 (300 mg) (N = 10) | Cohort 7 (150 mg) (N = 7) | Placebo (from Cohorts 1 and 2) (N = 7) | Placebo (Cohort 7) (N = 7) | All Subjects Dosed (N = 39) |
|---|---|---|---|---|---|---|---|
| Nervous system disorders | Moderate | 2 (25%) [2] | 3 (30%) [3] | 1 (14%) [1] | | | 6 (15%) [6] |
| | Mild | 2 (25%) [8] | 3 (30%) [6] | 4 (57%) [4] | 5 (71%) [7] | 4 (57%) [8] | 18 (46%) [33] |
| Dizziness | Mild | | | | 2 (29%) [4] | 2 (29%) [2] | 4 (10%) [6] |
| Headache | Moderate | 1 (13%) [1] | 2 (20%) [2] | 1 (14%) [1] | | | 4 (10%) [4] |
| | Mild | 2 (25%) [8] | 3 (30%) [6] | 2 (29%) [2] | 3 (43%) [3] | 3 (43%) [4] | 13 (33%) [23] |
| Lethargy | Mild | | | 1 (14%) [1] | | 1 (14%) [1] | 2 (5%) [2] |
| Migraine | Moderate | 1 (13%) [1] | 1 (10%) [1] | | | | 2 (5%) [2] |
| | Mild | | | | | 1 (14%) [1] | 1 (3%) [1] |
| Presyncope | Mild | | | 1 (14%) [1] | | | 1 (3%) [1] |
| Gastrointestinal disorders | Severe | 1 (13%) [1] | 1 (10%) [2] | | | | 2 (5%) [3] |
| | Moderate | 4 (50%) [5] | 6 (60%) [6] | | | | 10 (26%) [11] |
| | Mild | 2 (25%) [2] | 2 (20%) [2] | 3 (43%) [4] | 1 (14%) [1] | 3 (43%) [5] | 11 (28%) [14] |
| Abdominal pain | Severe | | 1 (10%) [2] | | | | 1 (3%) [2] |
| | Mild | | | | | 1 (14%) [1] | 1 (3%) [1] |
| Aphthous stomatitis | Mild | | | | | 1 (14%) [1] | 1 (3%) [1] |
| Change of bowel habit | Mild | | 1 (10%) [1] | | | | 1 (3%) [1] |
| Diarrhoea | Mild | | | 1 (14%) [1] | | 1 (14%) [1] | 2 (5%) [2] |
| Dry mouth | Mild | | | 1 (14%) [1] | | 1 (14%) [1] | 2 (5%) [2] |
| Gastrointestinal disorder | Moderate | | 2 (20%) [2] | | | | 2 (5%) [2] |
| Gastrointestinal sounds abnormal | Mild | | | | 1 (14%) [1] | | 1 (3%) [1] |
| Gastrooesophageal reflux disease | Mild | | | 1 (14%) [1] | | | 1 (3%) [1] |
| Lip dry | Mild | | | 1 (14%) [1] | | | 1 (3%) [1] |
| Vomiting | Severe | 1 (13%) [1] | | | | | 1 (3%) [1] |

TABLE 9

Time course of gastrointestinal/headache adverse events

| Count of TEAE_YN SI_type | Treatment | Week 1 | Week 2 | Week 3-4 | Week 5-6 | Week 7-8 | Week 9 | Grand Total |
|---|---|---|---|---|---|---|---|---|
| Gastro System Organ Class | peptide composition (Cohort 1) | 4 | 0 | 1 | 0 | 3 | 0 | 8 |
| | peptide composition (Cohort 2) | 8 | 0 | 0 | 2 | 0 | 0 | 10 |
| | peptide composition (Cohort 7) | 2 | 1 | 0 | 0 | 0 | 1 | 4 |

TABLE 9-continued

Time course of gastrointestinal/headache adverse events

| Count of TEAE_YN SI_type | Treatment | Week 1 | Week 2 | Week 3-4 | Week 5-6 | Week 7-8 | Week 9 | Grand Total |
|---|---|---|---|---|---|---|---|---|
| | Placebo (Cohort 1 and 2) | 0 | 0 | 0 | 1 | 0 | 0 | 1 |
| | Placebo (Cohort 7) | 1 | 0 | 2 | 0 | 2 | 0 | 5 |
| Gastro System Organ Class Total | | 15 | 1 | 3 | 3 | 5 | 1 | 28 |
| Headache | peptide composition (Cohort 1) | 1 | 3 | 3 | 1 | 1 | 0 | 9 |
| | peptide composition (Cohort 2) | 5 | 2 | 0 | 1 | 0 | 0 | 8 |
| | peptide composition (Cohort 7) | 1 | 1 | 0 | 0 | 0 | 1 | 3 |
| | Placebo (Cohort 1 and 2) | 1 | 1 | 0 | 1 | 0 | 0 | 3 |
| | Placebo (Cohort 7) | 2 | 2 | 0 | 0 | 0 | 0 | 4 |
| Headache Total | | 10 | 9 | 3 | 3 | 1 | 1 | 27 |
| Grand Total | | 25 | 10 | 6 | 6 | 6 | 2 | 55 |

Conclusions

The maximum tolerated dose in this study was 150 micrograms. Tolerance to the peptide composition was induced in 14 of 14 responsive subjects. Tolerance to gluten was induced in 6 of 8 responsive subjects. There was no conversion of negative to positive tTG serology and biopsy was not worsened by exposure to the peptide composition.

Figure 16:
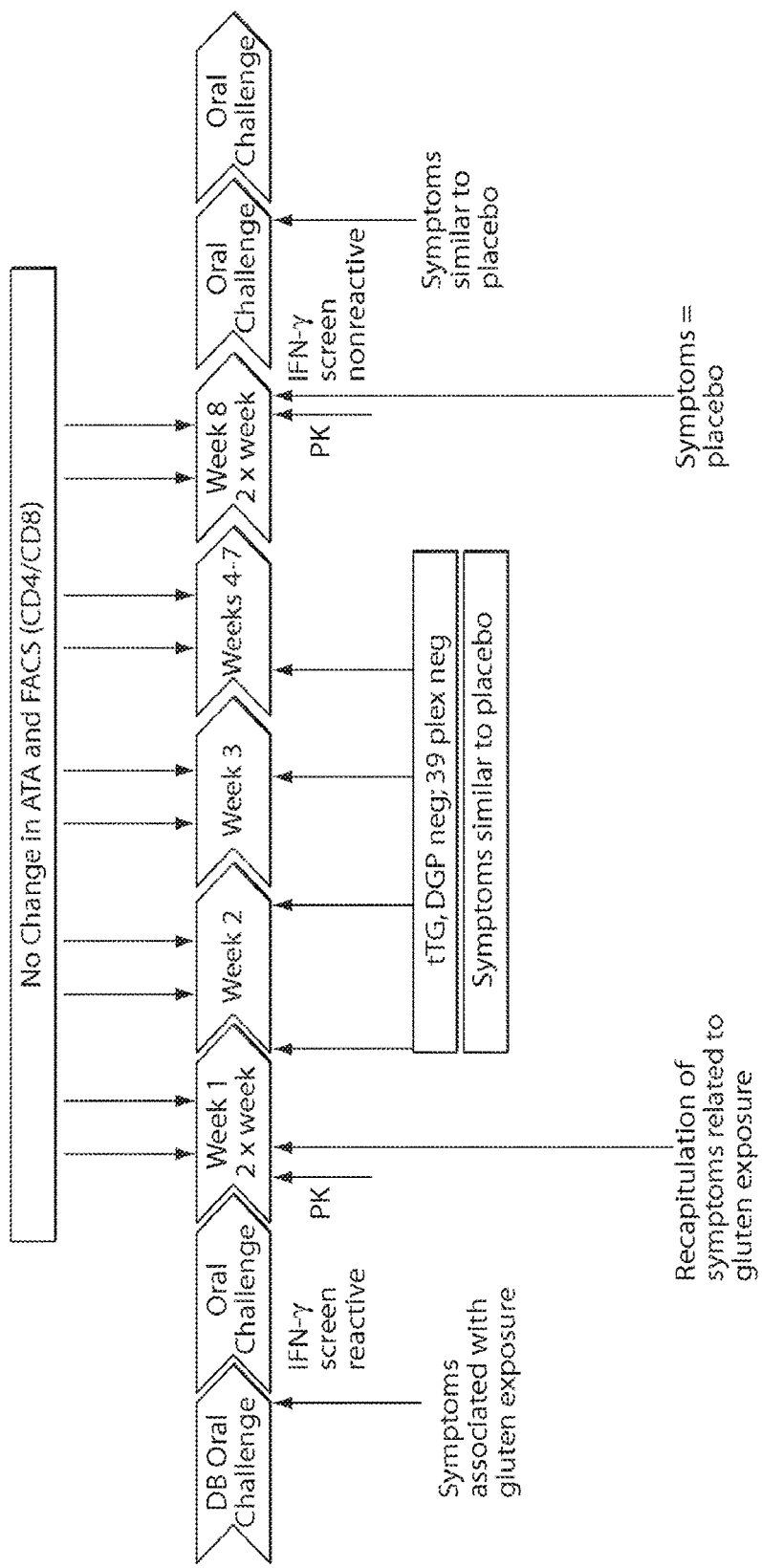
FIG. 16 is a diagram showing an exemplary time course for cohorts 1 and 2 (150 and 300 micrograms peptide composition, respectively).

A summary of the study as well as the assessments and further assessments performed during the study in Example 3 are shown in Table 10 below (which is split up into multiple tables). An exemplary time course for cohorts 1 and 2 is shown in FIG. 16.

TABLE 10

Study parameters and assessments

| | | | Visit 1-5 Double Blind Oral Challenge Visit | | | | |
|---|---|---|---|---|---|---|---|
| | | | V1 | | | V2 | V3 |
| | | | Day (S = screening, T = treatment) | | | | |
| Parameter | Notes | Sample | S-35 | S-34 | S-33 | S-30 | S-28 |
| Treatment: Peptide composition/ Placebo | | | | | | | |
| Oral challenge: Gluten/Placebo cookies | | | x | x | x | | x |
| IFN-γ Whole Blood Release Assay | Peptide composition- NIL pg/mL | IFN-γ WBRA Plasma-heparin | x | | | x | x |
| FACS | In PBMC | PBMC | x | | | | |
| ADA | Peptide composition IgG & IgA titer, reflex peptide 1-3 IgG & IgA | Serum | x | | | | |
| CD-serology | tTG-IgA (4 kits), DGP IgG & IgA (2 kits), & EmA | Serum | x | | | | |
| PK | 10 time points 0-6 hours. Only trough levels at V17 | Plasma-EDTA | | | | | |

TABLE 10-continued

Study parameters and assessments

| | | | |
|---|---|---|---|
| Histology-Score (Biopsy cohort) | Bulb, D1, D2 & D3 duplicate biopsies: Mod-Marsh Score | Biopsy | |
| Histology-Quantitative (Biopsy cohort) | Bulb, D1, D2 & D3 duplicate biopsies: IEL density/100 | Biopsy | |
| Histology-Quantitative (Biopsy cohort) | Bulb, D1, D2 & D3 duplicate biopsies: VH:CrD | Biopsy | |
| MAGPIX: In plasma | 38 cytokines and chemokines | Plasma-EDTA | x |
| MAGPIX: In each of 10 PK time course plasmas | 38 cytokines and chemokines | PK Plasma-EDTA x10 | |
| MAGPIX: Peptide composition-NIL response (150 mcg cohort only) | 38 cytokines and chemokines | IFN-γ WBRA Plasma-heparin | x      x |

| | Visit 1-5 Double Blind Oral Challenge | | | | | | Induction Phase (8 weeks of dosing) | |
|---|---|---|---|---|---|---|---|---|
| Parameter | S-27 | S-26 | V4 S-23 | V5 S-07 | V5.1 S-07 | V5.2 S-07 | Endoscopy Screening | V6 T + 01 | V7 T + 04 |
| Treatment: Peptide composition/ Placebo | | | | | | | | x | x |
| Oral challenge: Gluten/Placebo cookies | x | x | | | | | | | |
| IFN-γ Whole Blood Release Assay | | | x | x | x | x | | x | |
| FACS | | | x | | | | | x | |
| ADA | | | | | | | | x | |
| CD-serology | | | | | | | | x | |
| PK | | | | | | | | x | |
| Histology-Score (Biopsy cohort) | | | | | | | x | | |
| Histology-Quantitative (Biopsy cohort) | | | | | | | x | | |
| Histology-Quantitative (Biopsy cohort) | | | | | | | x | | |
| MAGPIX: In plasma | | | x | | | | | x | |
| MAGPIX: In each of 10 PK time course plasmas | | | | | | | | x | |
| MAGPIX: Peptide composition-NIL response (150 mcg cohort only) | | | x | | | | | | |

| | Induction Phase (8 weeks of dosing) | | | | | | | |
|---|---|---|---|---|---|---|---|---|
| Parameter | V8 T + 8 | V9 T + 11 | V10 T + 15 | V11 T + 18 | V12 T + 22 | V13 T + 25 | V14 T + 29 | V15 T + 32 |
| Treatment: Peptide composition/ Placebo | x | x | x | x | x | x | x | x |
| Oral challenge: Gluten/Placebo cookies | | | | | | | | |

TABLE 10-continued

| Study parameters and assessments | | | | | | | |
|---|---|---|---|---|---|---|---|
| IFN-γ Whole Blood Release Assay | x | | | x | | | |
| FACS | x | | | x | | | |
| ADA | x | | | x | | | |
| CD-serology | | | | | | | |
| PK | | | | | | | |
| Histology-Score (Biopsy cohort) | | | | | | | |
| Histology-Quantitative (Biopsy cohort) | | | | | | | |
| Histology-Quantitative (Biopsy cohort) | | | | | | | |
| MAGPIX: In plasma | x | | | x | | | |
| MAGPIX: In each of 10 PK time course plasmas | | | | | | | |
| MAGPIX: Peptide composition-NIL response (150 mcg cohort only) | | | | | | | |

| | Induction Phase (8 weeks of dosing) | | | | | | |
|---|---|---|---|---|---|---|---|
| Parameter | V16 T + 36 | V17 T + 39 | V18 T + 43 | V19 T + 46 | V20 T + 50 | V21 (EOT) T + 53 | Endoscopy Follow-up |
| Treatment: Peptide composition/ Placebo | x | x | x | x | x | x | |
| Oral challenge: Gluten/Placebo cookies | | | | | | | |
| IFN-γ Whole Blood Release Assay | | x | | | | x | |
| FACS | | x | | | | x | |
| ADA | | x | | | | | |
| CD-serology | | | | | | | |
| PK | | x | | | | x | |
| Histology-Score (Biopsy cohort) | | | | | | | x |
| Histology-Quantitative (Biopsy cohort) | | | | | | | x |
| Histology-Quantitative (Biopsy cohort) | | | | | | | x |
| MAGPIX: In plasma | | x | | | | x | |
| MAGPIX: In each of 10 PK time course plasmas | | | | | | x | |
| MAGPIX: Peptide composition-NIL response (150 mcg cohort only) | | | | | | | |

TABLE 10-continued

Study parameters and assessments

| | Post-treatment Double Blind Oral Challenge | | | | | | | | |
|---|---|---|---|---|---|---|---|---|---|
| Parameter | V22 T + 54 | T + 55 | T + 56 | V23 T + 59 | V24 T + 61 | T + 62 | T + 63 | V25 T + 66 | V26 (EOS) T + 88 |
| Treatment: Peptide composition/Placebo | | | | | | | | | |
| Oral challenge: Gluten/Placebo cookies | X | X | X | | X | X | X | | |
| IFN-γ Whole Blood Release Assay | X | | | X | X | | | X | X |
| FACS | | | | | | | | X | X |
| ADA | X | | | | | | | | X |
| CD-serology | X | | | | | | | | X |
| PK | | | | | | | | | |
| Histology-Score (Biopsy cohort) | | | | | | | | | |
| Histology-Quantitative (Biopsy cohort) | | | | | | | | | |
| Histology-Quantitative (Biopsy cohort) | | | | | | | | | |
| MAGPIX: In plasma | | | | | | | | X | X |
| MAGPIX: In each of 10 PK time course plasmas | | | | | | | | | |
| MAGPIX: Peptide composition-NIL response (150 mcg cohort only) | X | | | X | | | | | |

Example 4: Gastrointestinal Symptom Rating Scale (GSRS) Data

The GSRS is a validated diary tool used in Gastroesophageal Reflux Disease (GERD) studies. The GSRS scale is as follows:
1=no discomfort at all
2=minor discomfort
3=mild discomfort
4=moderate discomfort
5=moderately severe discomfort
6=severe discomfort
7=very severe discomfort The GSRS was used for all subjects described in Example 3 to keep track of symptoms. There were 6 questions on: bloating, diarrhea, hunger pain, nausea, pain, and rumbling. The GSRS was conducted daily (looking at past 24 hours) throughout the trial described in Example 3. The daily values were averaged for 6 days and the following were calculated: cohort means for gluten challenges, dosing period, and change from baseline is dosing period.

The symptom scores during dosing are shown in FIG. 6. The symptom scores during dosing as changed from baseline are shown in FIG. 7. The symptom scores during gluten challenge are shown in FIG. 8.

Generally, during dosing, symptoms increased from week −1 to week 1 with Cohorts 1 and 2 (150 micrograms and 300 micrograms with oral challenge, respectively) increasing more than Cohort 7 (150 microgram biopsy). During the course of dosing, the symptoms in all peptide composition cohorts (Cohorts 1, 2, and 7) decreased to where at week 8 there was no change from the week −1 baseline. For the gluten challenge, the symptom scores were higher for active gluten than placebo gluten both pre-dosing and post-dosing with the peptide composition or placebo. However, the mean scores were between 1 ("No symptoms at all") and 2 ("Minor symptoms").

Example 5: Biopsy Data

Biopsy data from the study in Example 3 is summarized below.

Small bowel biopsies were conducted at duodenal bulb and parts 1, 2, and 3 of jejunum. 2 biopsies were taken per area=8 pre-dose samples and 8 post-dose samples. Screening biopsies were all required to be Marsh-Oberhuber 0 or 1 for enrollment into the study. After collection of the post-treatment biopsy, H+E stained sections were re-assessed for Marsh-Oberhuber score. Villous height to crypt depth (VH/CrD) ratios were determined in well oriented sections. Intra-epithelial lymphocytes (IEL) per 100 epithelial cells were assessed in anti-CD3-stained slides.

The Marsh-Oberhuber classification (Oberhuber 1999) is shown in Table 11 below.

TABLE 11

| | Marsh-Oberhuber classification | | | | | |
|---|---|---|---|---|---|---|
| | Type 0 | Type 1 | Type 2 | Type 3a | Type 3b | Type 3c |
| Score | 0 | 1 | 2 | 3 | 4 | 5 |
| IEL* | <40 | >40 | >40 | >40 | >40 | >40 |
| Crypts | Normal | Normal | Hypertrophic | Hypertrophic | Hypertrophic | Hypertrophic |
| Villi | Normal | Normal | Normal | Mild atrophy | Marked atrophy | Absent |

Figure 9:
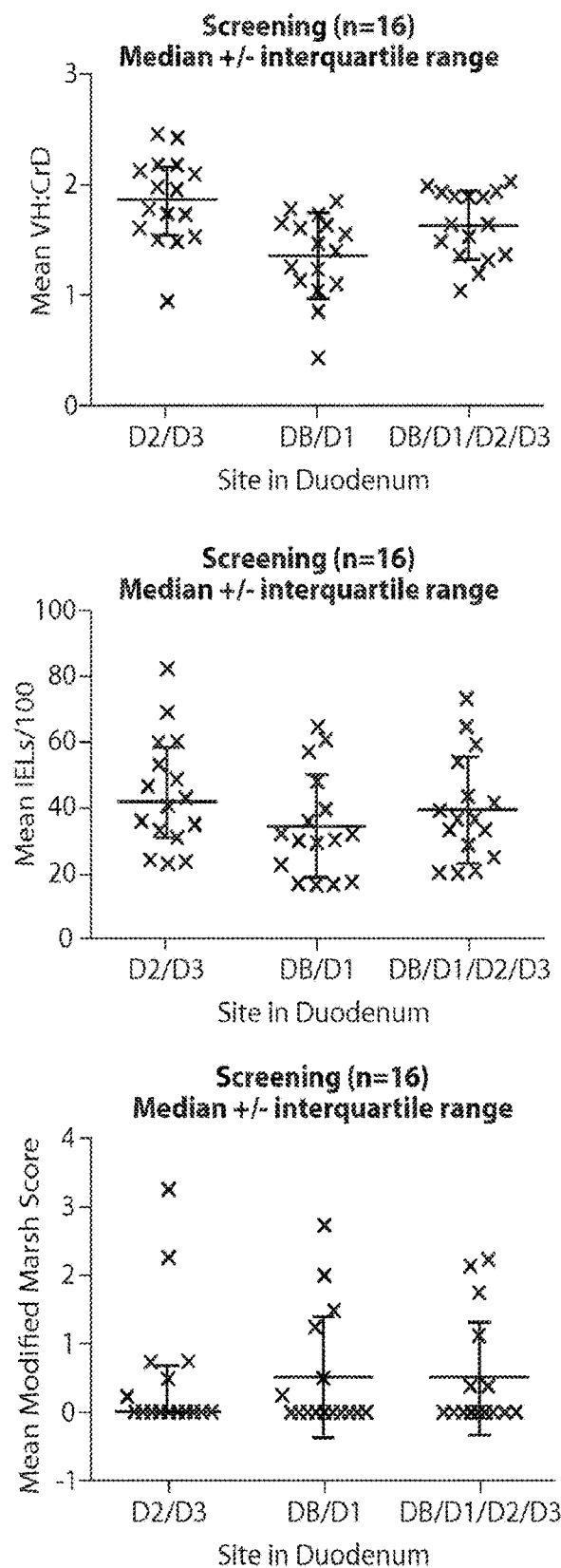
FIG. 9 is a series of graphs showing the mean villous height to crypt depth (VH:CrD) ratio at different sites in the duodenum.

*Numbers are given as IEL per 100 epithelial cells (counted from H + E stained biopsy sections The mean villous height to crypt depth (VH:CrD) is shown in FIG. 9. Two of the 16 screenees excluded as initial read of histology was scored as modified marsh 3 (villous atrophy and increased IEL count) indicating "active disease". At the end of the study, modified marsh score, VH:CrD (N>3) and IEL count per 100 epithelial cells was evaluated by observers blind to the subject number and timing of biopsy collection.

Figure 10:
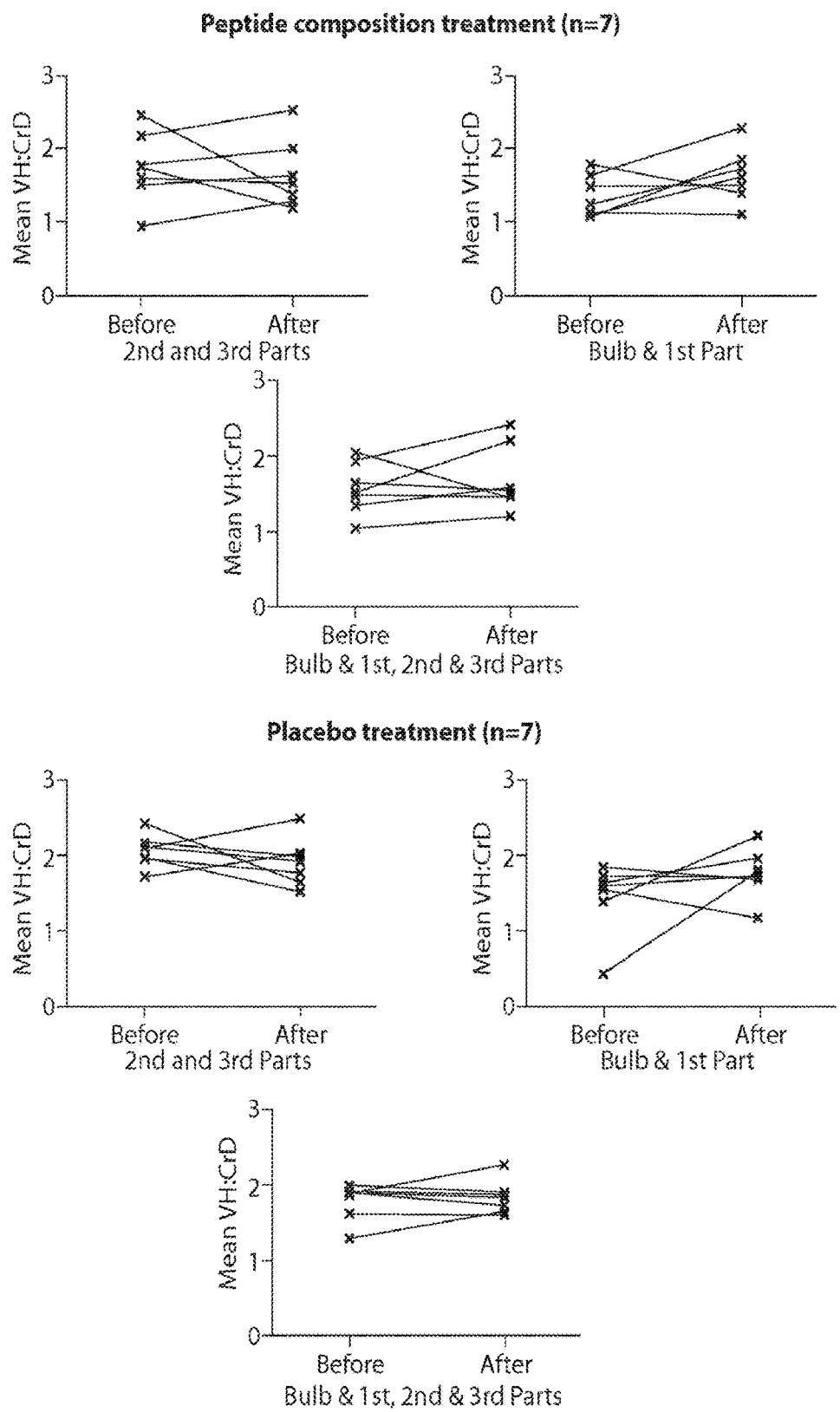
FIG. 10 is a series of graphs showing VH:CrD before and after treatment with peptide composition or placebo.
Figure 11:
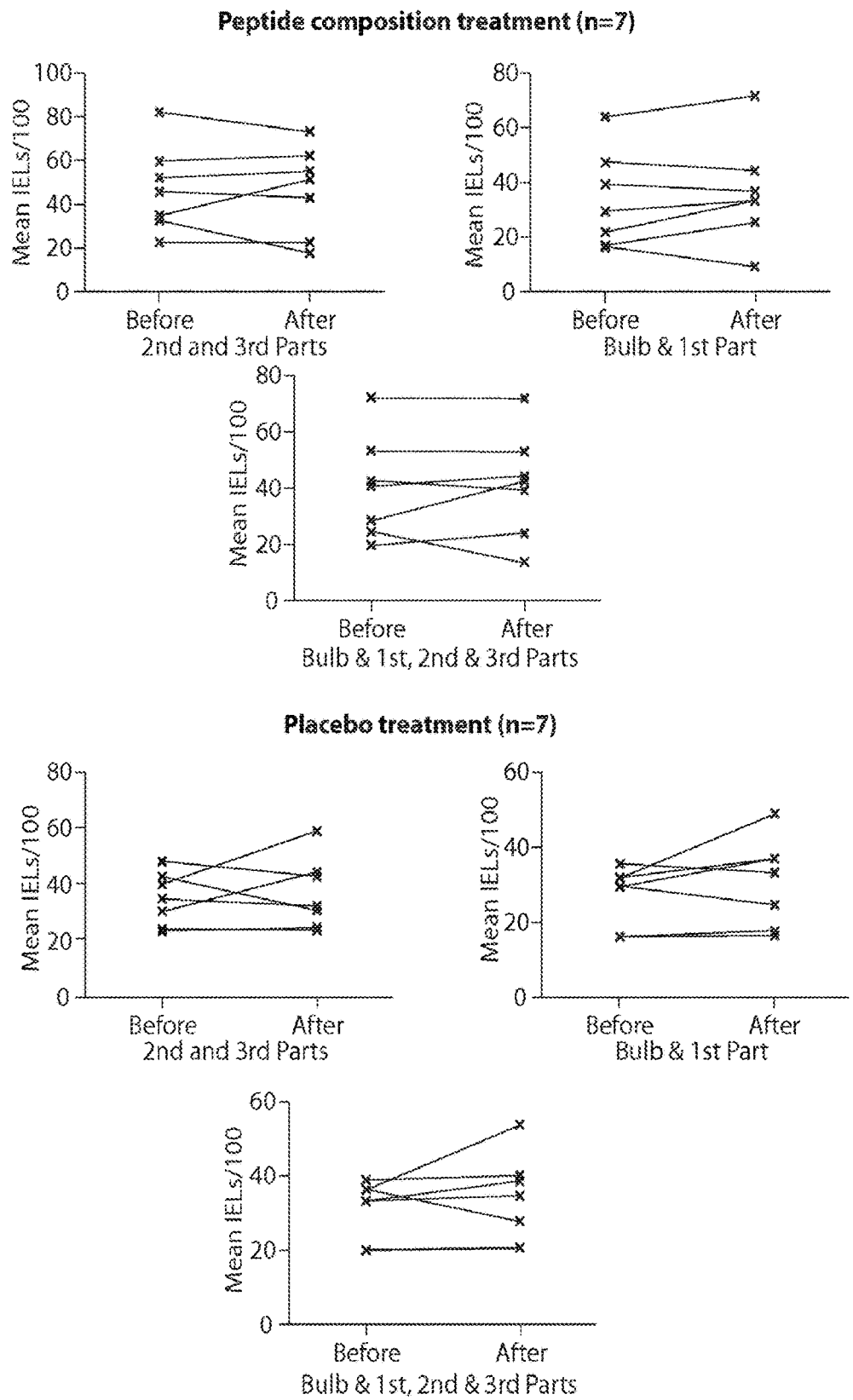
FIG. 11 is a series of graphs showing intraepithelial lymphocyte (IEL) count before and after treatment with peptide composition or placebo.
Figure 12:
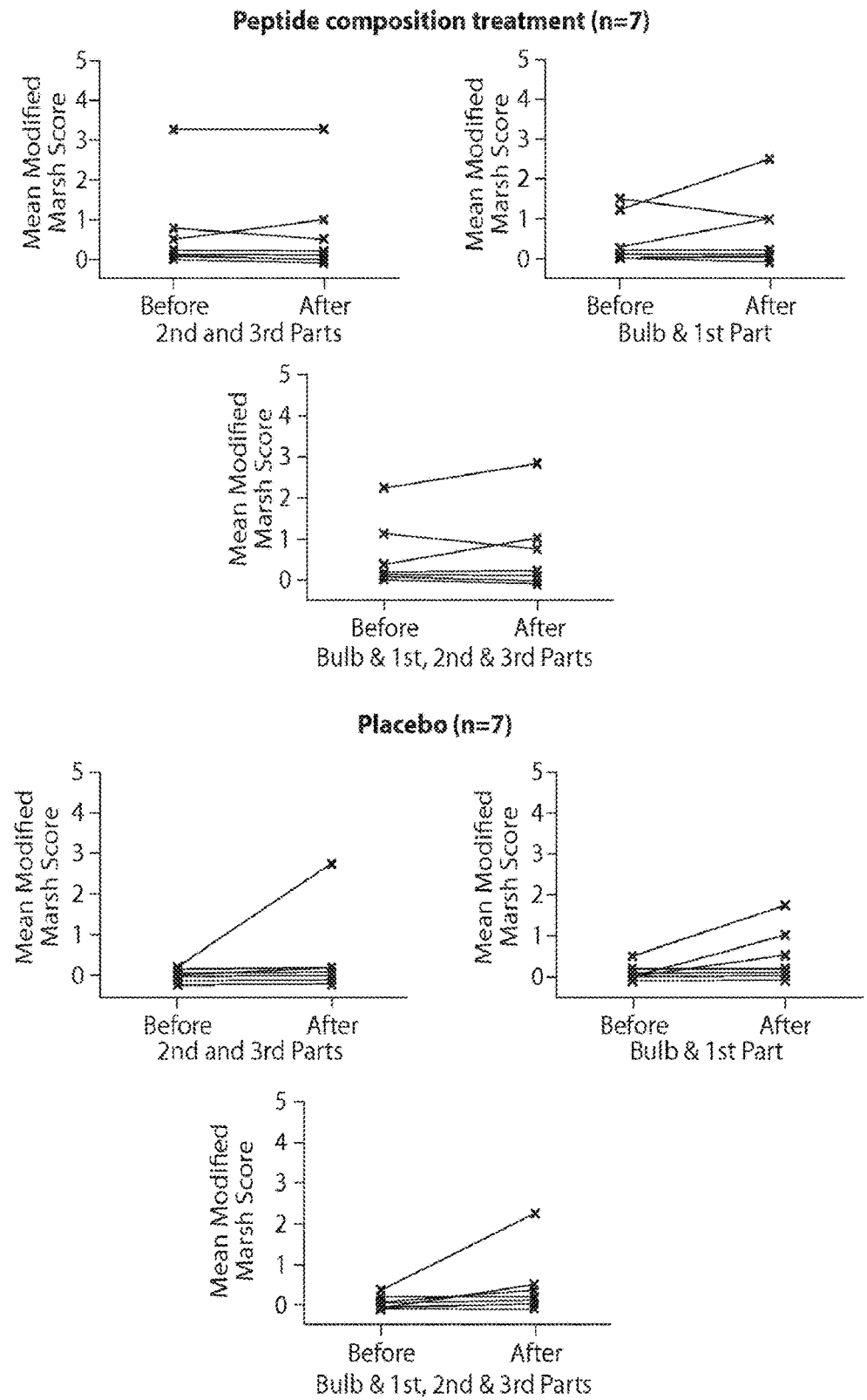
FIG. 12 is a series of graphs showing the modified marsh score before and after treatment with peptide composition or placebo.

It was found that there was no change in VH:CrD before and after treatment with peptide composition or placebo (FIG. 10, normal mucosal morphology shows VH:CrD as greater than 3). It was also found that there was no change in IEL count before and after treatment with peptide composition or placebo (FIG. 11, normal IEL count shows fewer than 20 per 100 epithelial cells). It was also found that there was no change in modified marsh score before and after treatment with peptide composition or placebo (FIG. 12, normal mucosa is scored 0, raised IELs 1, crypt hyperplasia 2, villous atrophy 3-5). The quantitative histology is summarized in Table 12 below.

and 1.92 after treatment, an IEL of 35 before treatment and 37 after treatment, and a Marsh score of 0.04 before treatment and 0.43 after treatment. It was determined that exposure to the peptide composition did not worsen the modified marsh score.

Example 6: Further Tolerance Assessments

The cohorts from Example 3 were analyzed using different ex vivo whole blood cytokine release assays to assess reactivity and tolerance to the peptide composition after treatment with the peptide composition or placebo. The subjects underwent a double-blind placebo-controlled gluten challenge pre- and post-treatment. To be reactive to the peptide composition, the subjects had to have an IFN-γ ELISA after contact with the peptide composition of >7.2 pg/mL above negative control (not contacted with the peptide composition) and a stimulation index of >1.25 or a MAGPIX ratio of peptide composition to negative control of

TABLE 12

| | VH:CrD AVG D2/D3 | VH:CrD AVG DB/D1 | VH:CrD AVG DB/D1/ D2/D3 | IEL/100 AVG D2/D3 | IEL/100 AVG DB/D1 | IEL/100 AVG DB/D1/ D2/D3 | Marsh AVG D2/D3 | Marsh AVG DB/D1 | Marsh AVG DB/D1/ D2/D3 |
|---|---|---|---|---|---|---|---|---|---|
| Peptide composition screen mean | 1.74 | 1.34 | 1.57 | 47.39 | 33.89 | 40.64 | 0.64 | 0.43 | 0.54 |
| Placebo screen mean | 2.07 | 1.46 | 1.79 | 34.89 | 27.21 | 31.05 | 0.04 | 0.07 | 0.05 |
| Peptide composition follow-up mean | 1.65 | 1.63 | 1.68 | 46.50 | 36.71 | 41.61 | 0.68 | 0.64 | 0.66 |
| Placebo Followup Mean | 1.92 | 1.76 | 1.84 | 36.82 | 30.68 | 33.75 | 0.43 | 0.46 | 0.45 |
| Peptide composition Followup Screen | −0.09 | 0.29 | 0.11 | −0.89 | 2.82 | 0.96 | 0.04 | 0.21 | 0.13 |
| Placebo Followup Screen | −0.15 | 0.30 | 0.05 | 1.93 | 3.46 | 2.70 | 0.39 | 0.39 | 0.39 |

The purpose of assessing biopsies was because tissue damage defines reactivation and results in complications. It was hypothesized that biopsies from part 2 and 3 of duodenum were probably cleanest since they do not contain Brunners glands as do bulb and part 1. In summary, the peptide composition cohort had a mean VH:CrD of 1.74 before treatment and 1.65 after treatment, an IEL of 47 before treatment and 47 after treatment, and a Marsh score of 0.64 before treatment and 0.68 after treatment. The placebo cohort had a mean VH:CrD of 2.07 before treatment >2. To be tolerant to the peptide composition, the subjects had to have net IFN-γ levels <7.2 pg/mL or stimulation index of <1.25 by ELISA and <2-fold elevation of IFN-γ, IL-2 or IP-10 by MAGPIX at visit 23. According to these criteria, it was found that 5 of 7 responsive subjects in Cohort 1 (150 micrograms) became non-reactive to the peptide composition (FIG. 13). It was found that 3 of 3 responsive subjects in Cohort 2 (300 micrograms) became non-reactive to the peptide composition (FIG. 14). It was found that 1 of 7 responsive subjects in Placebo Cohort (Cohorts 1 and 2 placebo) became non-reactive to the peptide composition (FIG. 15).

The cohorts were also analyzed using plasma cytokine levels. The plasma cytokine levels were measured at 37 time points pre- and post-first and last dose of peptide composition. For a subject to be tolerant to the peptide composition, they had to have less than a 2-fold increase after the last of peptide composition of IL-8 and MCP-1. It was found that 16 of 16 Cytokine Reactive Patients were tolerized to intradermal peptide composition, and peptide composition reactivity was abolished in 8 of 10 Patients treated with the peptide composition after oral gluten challenge. A summary of the change in tolerance/reactivity to the peptide composition is shown in Table 13.

TABLE 13

Tolerance/reactivity to the peptide composition

| Cytokines | Peptide composition reactive first dose cohort 1, 2, 7 | Peptide composition reactive last dose cohort 1, 2, 7 |
|---|---|---|
| IL-8 & MCP-1 (plasma) | 16/17 (vs. 0/7 in placebo arms) | 0/16 (vs. 0/7 in placebo arms) |
| Cytokines | Gluten Reactive Pre-treatment (V2/4) Cohort 1, 2 | Gluten Reactive Post-treatment (V23) Cohort 1, 2 |
| IFN-γ/IL-2/IP-10 ex vivo release (6 days after oral challenge) | 10/12 (vs. 7/7 in placebo arms) | 2/10 (vs. 6/7 in placebo arms) |

Peptide composition reactive T-cells in vivo => 2 fold plasma cytokine increase
Peptide composition reactive T-cells ex vivo => 7.2 pg/ml IFN-γ & SI >1.25 OR >2-fold increase in IFN-γ, IP-10 or IL-2

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for treating Celiac disease in a subject, the method comprising:
   administering to the subject:
   (a) a first peptide comprising the amino acid sequence ELQPFPQPELPYPQPQ (SEQ ID NO: 1), wherein the N-terminal glutamate is a pyroglutamate and the C-terminal glutamine is amidated;
   (b) a second peptide comprising the amino acid sequence EQPFPQPEQPFPWQP (SEQ ID NO: 2), wherein the N-terminal glutamate is a pyroglutamate and the C-terminal proline is amidated; and
   (c) a third peptide comprising the amino acid sequence EPEQPIPEQPQPYPQQ (SEQ ID NO: 3), wherein the N-terminal glutamate is a pyroglutamate and the C-terminal glutamine is amidated;
   wherein 50 micrograms of the first peptide and an equimolar amount of each of the second and third peptides are administered once or twice per week to the subject.

2. The method of claim 1, wherein the first, second and third peptides are in equimolar amounts in a composition, and the composition is administered to the subject.

3. The method of claim 2, wherein the first, second and third peptides are each in an amount of 50 micrograms in the composition.

4. The method of claim 1, wherein the first, second and third peptides are administered intradermally.

5. The method of claim 4, wherein the first, second and third peptides are administered as a bolus by intradermal injection.

6. The method of claim 1, wherein the first, second and third peptides are formulated as a sterile, injectable solution.

7. The method of claim 6, wherein the sterile, injectable solution comprises sodium chloride.

8. The method of claim 7, wherein the sodium chloride is a sterile sodium chloride solution with a sodium chloride concentration of 0.9% USP.

9. The method of claim 1, wherein, when the administration is twice a week, the first, second and third peptides are administered for four weeks.

10. The method of claim 1, wherein the first, second and third peptides are administered for three weeks.

11. The method of claim 1, wherein the subject is HLA-DQ2.5 positive.

12. The method of claim 1, wherein the method further comprises assessing immune tolerance after administration of the first, second and third peptides.

13. The method of claim 12, wherein assessing immune tolerance comprises measuring a T cell response to gluten and/or to the first, second and third peptides in a sample comprising T cells from the subject.

14. The method of claim 13, wherein measuring the T cell response comprises contacting the sample with gluten and/or the first, second and third peptides and measuring the T cell response in the sample after the contacting.

15. The method of claim 14, wherein the T cell response is measured by measuring a level of IFN-$\gamma$.

16. The method of claim 15, wherein measuring the level of IFN-$\gamma$ comprises an immuno-based assay.

17. The method of claim 1, wherein the first, second and third peptides are administered for eight weeks.

18. The method of claim 1, wherein the subject is on a gluten-free diet.

19. The method of claim 16, wherein the immuno-based assay comprises an ELISA or a multiplex bead-based assay.

20. The method of claim 1, wherein administering the first, second and third peptides induces immune tolerance to gluten in the subject.

21. The method of claim 20, wherein administering the first, second and third peptides induces immune tolerance to wheat, barley and rye in the subject.

\* \* \* \* \*